[19] United States Patent
Vierling, Jr.

[11] Patent Number: 5,866,695
[45] Date of Patent: Feb. 2, 1999

[54] SOYBEAN PEROXYDASE GENE FAMILY AND AN ASSAY FOR DETECTING SOYBEAN PEROXIDASE ACTIVITY

[75] Inventor: Richard A. Vierling, Jr., Lafayette, Ind.

[73] Assignee: Indiana Crop Improvement Association, Lafayette, Ind.

[21] Appl. No.: 868,577

[22] Filed: Jun. 4, 1997

Related U.S. Application Data

[63] Continuation-in-part of Ser. No. 671,320, Oct. 27, 1995.
[51] Int. Cl.$^6$ .............................. C07H 21/04; C12N 9/08
[52] U.S. Cl. .................. 536/23.2; 536/23.6; 536/24.1; 435/192
[58] Field of Search ................... 536/23.2, 23.6, 536/24.1; 435/192

*Primary Examiner*—Robert A. Wax
*Assistant Examiner*—Elizabeth Slobodyansky
*Attorney, Agent, or Firm*—Rothwell, Figg, Ernst & Kurz

[57] ABSTRACT

The present invention relates to the genomic DNA and promoters of soybean peroxidases and their use as promoters for producing transgenic plants, including transgenic soybeans. The invention also relates to immunoassays or oligouncleotide assays which utilize soybean peroxidase as a marker. The invention further relates to the use of third antibody, an anti-soybean peroxidase antibody, in immunoassays. Soybean peroxidase may be bound to the anti-soybean peroxidase antibody prior to binding of this antibody with the second antibody (anti-antibody) in the assay. Alternatively, the anti-soybean peroxidase antibody is bound to the second antibody (anti-antibody) and then the soybean peroxidase bound by its specific antibody.

2 Claims, 21 Drawing Sheets

```
                                              sEP a1 ATG GGA AGC
                                              sEP a2 ... ... ...
                                                  p1  M   G   S
                                                  p2  .   .   .
AAC TTG AGG TTT TTG AGT CTT TGC CTC TTG GCA TTG ATT GCA TCG ACT CAT GCT
... ..C ... ... ... ... ... ... ... ... ... ... ... ..A ..C ... ... ...
 N   L   R   F   L   S   L   C   L   L   A   L   I   A   S   T   H   A   -1
 .   F   .   .   .   .   .   .   .   .   .   .   .   .   .   .   .   .
CAA CTT CAG CTT GGT TTT TAT GCT AAC AGT TGC CCA AAA GCA GAG CAA ATT GTT
... ... ... ... ... ... ... ..C ..G ... ... ... ..C ..T ... ... ..C ...
 Q   L   Q   L   G   F   Y   A   N   S   C   P   K   A   E   Q   I   V   18
 .   .   .   .   .   .   .   .   K   .   .   .   .   N   .   .   .   .
TTG AAA TTT GTT CAT GAC CAT ATC CAC AAT GCT CCA TCA CTA GCA GCA GCA TTA
... ... ... ..C ... ... ... ... ... ... ... ... ... ... ... ... ... ..G
 L   K   F   V   H   D   H   I   H   N   A   P   S   L   A   A   A   L   36
 .   .   .   .   .   .   .   .   .   .   .   .   .   .   .   .   .   .
ATA AGA ATG CAC TTT CAT GAC TGT TTT GTA AGG GGA TGT GAT GCA TCA GTC CTT
... ... ... ..C ... ... ... ... ... ... ... ... ... ... ... ... ... ...
 I   R   M  │H   F   H   D   C   F   V │ R   G   C   D   A   S   V   L   54
 .   .   . │.   .   .   .   .   .   . │ .   .   .   .   .   .   .   .
CTG AAC TCA ACA ACC AAT CAG GCT GAG AAG AAT GCT CCT CCA AAT CTC ACA GTA
... ... ... ... ... ..A ... ..A ... ... ... ... ... ... ... ... ... ...
 L   N   S   T   T   N   Q   A   E   K   N   A   P   P   N   L   T   V   72
 .   .   .   .   .   .   .   .   .   .   .   .   .   .   .   .   .   .
AGA GGC TTT GAC TTC ATT GAC AGA ATA AAG AGC CTT GTT GAA GCT GAA TGC CCT
... ... ... ... ... ... ... ... ... ... ... ... ..G ..A ... ... ... ...
 R   G   F   D   F   I   D   R   I   K   S   L   V   E   A   E   C   P   90
 .   .   .   .   .   .   .   .   .   .   .   .   .   .   .   .   .   .
GGT GTG GTC TCT TGT GCT GAT ATC CTC ACT TTG GCT GCC AGA GAC ACT ATT GTA
... ... ... ... ... ... ... ... ... ..T ... ... ... ... ... ... ... ...
 G   V   V   S   C   A   D   I   L   T   L   A │ A   R   D   T   I   V   108
 .   .   .   .   .   .   .   .   .   .   .   S │ .   .   .   .   .   .
GCC ACA GGT GGA CCT TTT TGG AAA GTT CCA ACT GGT CGA AGG GAT GGG GTC GTC
... ... ... ..A ... ... ... ... ..A ... ... ..A ... ... ..A ... ... A..
 A   T   G   G   P   F   W   K   V   P   T   G   R   R   D   G   V   V   126
 .   .   .   .   .   .   .   .   .   .   .   .   .   .   .   .   .   I
TCT AAC TTG ACG GAA GCC AGA AAT AAC ATT CCT GCT CCA TCT TCC AAC TTT ACC
... ... ... ... ... ... ..G ... ... ... ... ... ... ..T ... ... ... ...
 S   N   L   T   E   A   R   N   N   I   P   A   P   S   S   N   F   T   144
 .   .   .   .   .   .   .   D   .   .   .   .   .   .   .   .   .   .
```

FIG. 5A

```
ACC CTA CAA ACA CTC TTT GCT AAC CAA GGA CTT GAT TTG AAG GAC TTG GTC CTG
... ... ... ... ... ... ..C ... ... ... ... ... ... ... ... ... ... ...
 T   L   Q   T   L   F   A   N   Q   G   L   D   L   K  |D   L   V   L| 162
 .   .   .   .   .   .   .   .   .   .   .   .   .   .   .   .   .   .
CTC TCT GGT GCT CAC ACA ATT GGT ATC GCT CAT TGC TCA TCA TTA TCA AAC CGG
... ... ... ... ... ... ... ... ... ... ... ... ... ..G ... ... ... ..C
|L   S   G   A   H   T   I|  G   I   A   H   C   S   S   L   S   N   R  180
 .   .   .   .   .   .   .   .   .   .   .   .   .   .   .   .   .   .
TTG TTC AAT TTC ACT GGC AAG GGT GAT CAA GAC CCG TCA CTA GAT AGT GAA TAT
... ... ... ... ... ... ... ... ... ... ... ... ..T ..C ... ... ... ...
 L   F   N   F   T   G   K   G   D   Q   D   P   S   L   D   S   E   Y  198
 .   .   .   .   .   .   .   .   .   .   .   .   .   .   .   .   .   .
GCT GCA AAT TTG AAA GCA TTC AAG TGC ACA GAC CTC AAC AAG TTG AAC ACC ACA
... ... ... ...C.. ... ..C ... ... ... ... ..G ... ... ..T ... ... ...
 A   A   N   L   K   A   F   K   C   T   D   L   N   K   L   N   T   T  216
 .   .   .   .   .   .   .   .   .   .   .   .   .   .   .   .   .   .
AAA ATT GAG ATG GAC CCT GGA AGT CGC AAG ACA TTT GAT CTT AGC TAC TAT AGT
... ... ... ... ... ... ... ... ... ... ... ... ... ... ... ... ... ...
 K   I   E   M   D   P   G   S   R   K   T   F   D   L   S   Y   Y   S  234
 .   .   .   .   .   .   .   .   .   .   .   .   .   .   .   .   .   .
CAC GTT ATT AAG AGA AGG GGT CTA TTT GAG TCA GAT GCT GCA TTA TTG ACT AAC
... ... ... ... ... ... ... ... ... ... ... ... ... ..G ... ..A ... ...
 H   V   I   K   R   R   G   L   F   E   S   D   A   A   L   L   T   N  252
 .   .   .   .   .   .   .   .   .   .   .   .   .   .   .   .   .   .
TCA GTT ACA AAG GCA CAA ATC ATC CAA TTG CTT GAA GGG TCA GTT GAA AAT TTC
... ... ... ... ...G... ... ..T ..G ... ... ... ... ... ... ... ... ...
 S   V   T   K   A   Q   I   I   Q   L   L   E   G   S   V   E   N   F  270
 .   .   .   .   .   .   .   .   E   .   .   .   .   .   .   .   .   .
TTT GCT GAG TTT GCA ACC TCC ATC GAG AAA ATG GGA AGA ATT AAT GTG AAG ACA
... ... ... ... ... ... ... ..G ... ... ... ... ... ... ... ... ... ...
 F   A   E   F   A   T   S   I   E   K   M   G   R   I   N   V   K   T  288
 .   .   .   .   .   .   .   M   .   .   .   .   .   .   .   .   .   .
GGC ACA GAA GGA GAG ATC AGG AAG CAT TGT GCA TTT ATA AAT AGC TAA
..G ... ... ... ... ... ... ... ... ... ... ... ..C ... ... ...
 G   T   E   G   E   I   R   K   H   C   A   F   I   N   S  end
 .   .   .   .   .   .   .   .   .   .   .   .   L   .   .  end
```

FIG. 5B

```
                                        sEP b1  ATG GCT GTC ATG
                                        sEP b2  ... ... ... ...
                                        p3       M   A   V   M
                                        p4       .   .   .   .
GGT GCA TTC TTG AAT TTG ATC ATC *** TTT TCA GTA GTC TCT ACA ACA GGC AAG
... ... ... ... ... ... ... ... ATG ... ... ... ... ... *** ... ...
 V   A   F   L   N   L   I   I   *   F   S   V   V   S   T   T   G   K   -1
 .   .   .   .   .   .   .   .   M   .   .   .   .   .   *   .   .   .
TCA CTG AGC TTA AAC TAC TAT GCA AAA ACA TGC CCT AAT GTG GAG TTC ATT GTT
... ... ... ... ... ... T.. ... ... ... ... G.. ... ... A.G ... ... ...
 S   L   S   L   N   Y   Y   A   K   T   C   P   N   V   E   F   I   V   18
 .   .   .   .   .   .   .   S   .   .   .   D   .   .   C   .   .   .
GCC AAG GCA GTA AAG GAT GCC ACT GCT AGG GAC AAA ACT GTT CCA GCA GCA ATT
... ... ... ..G ... ... ... ... ... ... ... ... ... ... ..T ... C.. ...
 A   K   A   V   K   D   A   T   A   R   D   K   T   V   P   A   A   I   36
 .   .   .   .   .   .   .   .   .   .   .   .   .   .   .   .   .   L
CTG CGA ATG CAC TTC CAT GAT TGT TTC GTT CGG GGG TGT GAT GCC TCT GTG CTG
... ... ... ... ... ... ..C ... ... ... ... ... ... ..G ... ... ... ...
 L   R   M  |H   F   H   D   C   F   V|  R   G   C   D   A   S   V   L   54
 .   .   .  |.   .   .   .   .   .   .|  .   .   G   .   .   .   .   .
CTA AAT TCA AAA GGA AAC AAC AAA GCA GAA AAA GAC GGG CCA CCA AAT GTT TCT
... ... ... ..G ... ... ... ... ... ..T ... ... ... ... ... ... ... ...
 L   N   S   K   G   N   N   K   A   E   K   D   G   P   P   N   V   S   72
 .   .   .   .   .   S   .   .   .   .   .   .   .   .   .   .   .   .
TTG CAT GCA TTC TAT GTC ATT GTA GCA GCA AAG AAA GCA CTA GAA GCT TCA TGC
... ... ... ... ... ..AT ... ..G ... ... ... ... ... ... ... ... ... ...
 L   H   A   F   Y   V   I   V   A   A   K   K   A   L   E   A   S  |C   90
 .   .   .   .   .   .   .   D   .   .   .   .   .   .   .   .   .  |.
CCT GGT GTG GTC TCT TGT GCT GAC ATC CTT GCT CTG GCA GCA AGG GTC GCA GTT
..A ... ... ... ... ... ... ... ... ... ... A.. ... ... ..AT ... ...
 P   G   V   V   S   C   A   D   I   L   A   L   A|  A   R   V   A   V   ##
 .   .   .   .   .   .   .   .   .   .   .   .   .|  .   D   .   .
TTT CTG TCA GGA GGA CCT ACA TGG GAT GTT CCT AAA GGA AGA AAG GAT GGT AGA
... ... ... ... ... ... ..AA ... ... ... ... ... ... ... ... ..C ...
 F   L   S   G   G   P   T   W   D   V   P   K   G   R   K   D   G   R   ##
 .   .   .   .   .   .   .   .   E   .   .   .   .   .   .   .   .   .
ACA TCT AAA GCC AGT GAA ACC AGA CAA TTG CCA GCA CCA ACC TTC AAC TTA TCA
... ... ... ..C ... ... ... ... ..A ... ... ... ... ... ... ... ... ...
 T   S   K   A   S   E   T   R   Q   L   P   A   P   T   F   N   L   S   ##
 .   .   .   .   .   .   .   .   .   .   .   .   .   .   .   .   .   .
```

FIG. 6A

```
CAA CTG CGG CAA AGT TTC TCT CAA AGA GGA CTG TCA GGG GAA GAC CTG GTA GCT
... ... ... ... ... ..C ... ... ... ... ... ... ... ... ... ... ...
 Q   L   R   Q   S   F   S   Q   R   G   L   S   G   E  │D   L   V   A │ ##
 .   .   .   .   .   .   .   .   .   .   .   .   .   .  │.   .   .   . │
CTG TCA GGG GGG CAC ACT TTG GGT TTC TCT CAC TGC TCA TCT  TTC AAG AAC AGA
... ... ... ... ... ... ... ... ... ... ... ... ... ... ... ... ... ...
│L   S   G   H   T │ L   G   F   S   H   C   S   S   F   K   N   R   ##
 .   .   .   .   .   .   .   .   .   .   .   .   .   .   .   .   .
ATC CAC AAC TTC AAT GCA ACA CAT GAT GTT GAC CCT TCA TTA AAT CCA TCA TTT
... ... ... ... ... ..T ... ... ... .AA ... ... ... ... ... ... ... ...
 I   H   N   F   N   A   T   H   D   V   D   P   S   L   N   P   S   F   ##
 .   .   .   .   .   .   .   E   .   .   .   .   .   .   .   .   .
GCA GCA AAA CTG ATC TCA ATT TGT CCA CTA AAA AAT CAG GCA AAA AAT GCA GGC
...A... ... ... ... ..A ... ... ... ... ... ... ... ... ... ... ... ...
 A   A   K   L   I   S   I   C   P   L   K   N   Q   A   K   N   A   G   ##
 .   T   .   .   .   .   .   .   .   .   .   .   .   .   .   .   .   .
ACC TCT ATG GAC CCT TCA ACA ACA ACT TTT GAT AAT ACA TAT TAC AGG TTG ATC
... ... ... ... ... ... ... ... ... ... ... ... ... ... ... ... ... ...
 T   S   M   D   P   S   T   T   T   F   D   N   T   Y   Y   R   L   I   ##
 .   .   .   .   .   .   .   .   .   .   .   .   .   .   .   .   .   .
CTC CAA CAG AAA GGC TTG TTT TCT TCT GAT CAA GTT TTG CTT GAC AAC CCA GAC
... ... ... ... ... ... ... ... ... ... ... ... ... ... ... ... ... ...
 L   Q   Q   K   G   L   F   S   S   D   Q   V   L   L   D   N   P   D   ##
 .   .   .   .   .   .   .   .   .   .   .   .   .   .   .   .   .   .
ACT AAA AAT CTG GTT ACA AAG TTT GCC ACC TCA AAA AAG GCT TTT TAT GAG GCT
... ... ... ... ... G.G ... ... ... ... ... ... ... ... ... ... ..C ...
 T   K   N   L   V   T   K   F   A   T   S   K   K   A   F   Y   E   A   ##
 .   .   .   .   .   A   .   .   .   .   .   .   .   .   .   .   D   .
TTT GCG AAG TCC ATG ATC AGA ATG AGT AGC TAC AAT GGT GGA CAG GAG GTT AGA
... ... ... ... ... ..A ... ... ... ... AT. ... ... ... ... ... ... ...
 F   A   K   S   M   I   R   M   S   S   Y   N   G   G   Q   E   V   R   ##
 .   .   .   .   .   .   K   .   .   I   .   .   .   .   .   .   .
AGG ACT GCA GAA TGA
... ... ... ..G ...
 R   T   A   E  end
 .   .   .   .  end
```

FIG. 6B

Dot Blot Comparison of 3 antibody SBP and 2 antibody HRP systems

Western Blot A, a 2 antibody system using Horseradish Peroxidase
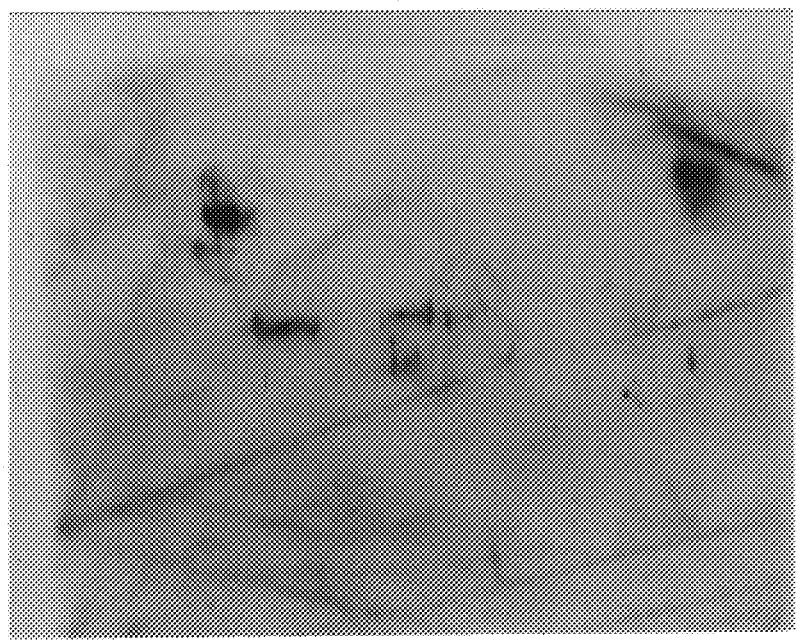
MWS  1   2   3   4   5   6   7   MWS
Western Blot B, a 3 antibody system using Soybean Peroxidase-Antiperoxidase
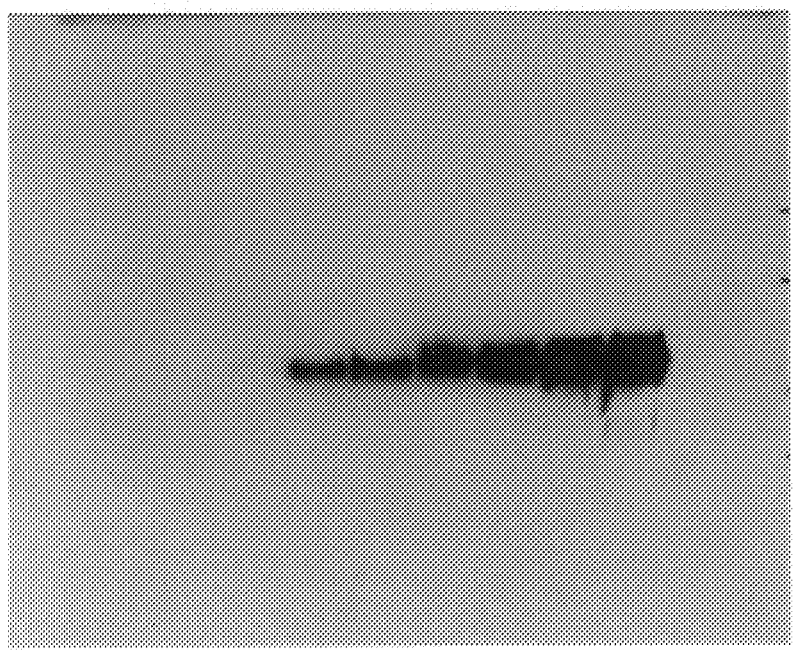
Lane1= .25ug Fetuin
Lane2= .50ug Fetuin
Lane3= 1ug Fetuin
Lane4= 2ug Fetuin
Lane5= 4ug Fetuin
Lane6= 8ug Fetuin
MWS  1   2   3   4   5   6   7   MWS
Lane 7 = 16ug Fetuin
MWS = Kaleidoscope Molecular
Weight Standard
FIG. 13

```
   1  TCAATGTCAG AATGATACTG ACAGATCTAA TTTCGGTTAA TTTGATTACT
  51  AATTAGTAGG TGCCAGTGGC ATAAATTGAA TAAGAAATAA AAATAATTCA
 101  TTATCAATTC AAATGAAGGA AAAATATATT GTGTCAAAAG GATATTAATT
 151  ATCAAGATTC AAAGGAAAAA ATAGTATACT CTTTTTTATA AATACACTAC
 201  TGAGTAATTT AACCAAATTT AAATTATAAT TTTAATGCTC AGTTTACTTC
 251  AATGGCTATA CCTTTTTTTT ATATATTCAA TGGCTATACC TATAAATTGT
 301  AATATTCAAG CATTGTTTTA ATGGAAGCAA ACAAGGCATC ACATATGGCT
 351  AGGAAGAATT GAACAAAAAC AAATTAGCTA CATACATTAA GCTCTTAATA
 401  TTATAAAAAC ATGCCGATGA TATATGTCCA TAGATTTCAA GGGAGCTAAT
 451  ACCGGAAAGT GTCAAGGATT TATACTTTAC AGCTAAAGTT TCAGTCTCAA
 501  AGAAAATGAT GACACTGTAT CATTGAGCAG ACACAATGAG TTACATCACA
 551  AAACCAGCCT GTAGGGATAC ATGACTCATA TTCCTTGTCA AATATCGCTG
 601  CCTCAATGTG CATAGCGATT ATAGTAATGG ATTCACAGTA AAGGAGCAGG
 651  TAAGCCAATT TTTTATTCTT AAATTCCCTG TTGAGACTAC ATTATATTTT
 701  TGAATTGCGA GATATTCAAG GATTACTTGT TATATATGTT AAGCCGCCGC
 751  ATACTGTTTA AAGTATTAAT GATATATCAT TGTTACTATA AAATATTTTT
 801  ACACAATGCA AGGTAAATAT TTCTATTACA TGTTGACATA AAAATATCTT
 851  ACGTAAACTA AACTAAACTC TTGTTTAAAA TGGTACTAGT ATCTATACAA
 901  CGAGATTAAA GCTACAAAAA TATGATACAA AGAGGGAGAT TTTGTATAGT
 951  ATCCTATGCT TGAAGAACGT ATCAACATCC AGTATCTCGA AAATTCAGTA
1001  CTAAAATGTA AAATCTATTG ATGTGTACTG AAGGATTCAG AAATTCAACT
1051  ATTTTGAACT CGCTGTATAT TAATTTGTCC ATATAAGGTC ACAGCAGCCA
1101  ACTAATCATT TTTTTATTAG AGACTAGATA CAATTATTAC ATGCAAATGG
1151  ATAATAAAGT AGCATGTAGC ATCACCTTAT CGCACATGTT AGTTAGCTGC
1201  ATGGACCATC TGTATGATTT GTGATGTGTC TTGTAGCTTA ACTTAAGCAC
1251  TATATATCAC TGATCAGTGT TGTGGAAACA GCGAAGAGAA ATGAAATTGC
1301  CTCTTTCAAG AAGCATCTGA GTGTTTACTA TTTTGTACTA TATTTATATA
```

Figure 14A

1351 TAGTCACTCA AGCTTCTAGG ATTTCTGCCT GCTGCATCAA AATGGGAAGC

1401 AACTTGAGGT TTTTGAGTCT TTGCCTCTTG GCATTGATTG CATCAACTCA

1451 TGCTCAACTT CAGCTTGGTT TTTATGCTAA CAGTTGCCCA AAAGCAGAGC

1501 AAATTGTTTT GAAATTTGTT CATGACCATA TCCACAATGC TCCATCACTA

1551 GCAGCTGCAT TAATAAGAAT GCACTTCCAT GACTGTTTTG TAAGGGTATG

1601 TGGTTCAAGC CTATAATTTT CTTTCATTTT TTACTTAACA AGTACCATAT

1651 ATGTTAGATT AAAGAACTAA CTAAGATGAA GTATTTCAGG GATGTGATGC

1701 ATCAGTCCTT CTGAACTCAA CAACCAATCA GGCTGAGAAG AATGCTCCTC

1751 CAAATCTCAC AGTAAGAGGC TTTGACTTCA TTGACAGAAT AAAGAGCCTT

1801 GTTGAAGCTG AATGCCCTGG TGTGGTCTCT TGTGCTGATA TCCTCACTTT

1851 GGCTGCCAGA GACACTATTG TAGCCACAGT AAGTACTCAA TTGCTATCAG

1901 GAAAATCTTA AGAGTATAAG CACAACTTCT GCTTCACCTT TATATCTTTA

1951 CACTTCTTTT TGAGAACAAG ATGACCCATT TGCTGGTTTA TGCCATTACT

2001 GACATTGGTG TTCAGGGTGG ACCTTTTTGG AAAGTTCCAA CTGGTCGAAG

2051 GGATGGGGTC GTCTCTAACT TGACGGAAGC CAGAAATAAC ATTCCTGCTC

2101 CATTTTCCAA CTTCACCACC CTACAGACAC TCTTTGCTAA CCAAGGACTT

2151 GATTTGAAGG ACTTGGTCCT GCTCTCTGGT ATCATTTATG AAACAAATCC

2201 TAAGCATTAT TGTTGAAAGA CTAACACGTT TTTGAGTCCC TCATGGTAAC

2251 GCCAGGTTTC CAGTCACGAC GTTGTAAAAC GACGGCCAGT GAGCGCGCAG

2301 TAATACGACT CACTATAGGC GAATTGGAGC TCCAGCGGTG GCGGCCGCTC

2351 TAGAACTAGT GGATCCCCCG GGCTGCAGGT TTTCGATATC AAGCTTATCG

2401 ATACCGTCGA CACCTCGAGT TGGAAATATG TCTAAATATC TGCAATTTCA

2451 ACATGAATAA TTTATTTTTT AGGAATTTAT TAACTACATT TTAAATTTTC

2501 AGGATATTGA TTTGATAATT CTTATTATTT AGACTTTAGG ACACTATCAG

2551 TTTGTTTAAT TTCAAGGTTA AGATGTGTTA TATTTTGAAT TTTGCATTAC

2601 ATTATTTCAT TTTAAAAAAT AAAACCAACA AATTGGCATG AATTATACAT

2651 TGTTCTTGGG CTTGTAATGA GCAAGAGTTC AAATTGTTTC AGGTGCTCAC

Figure 14B

```
2701  ACAATTGGTA TCGCTCATTG CTCATCATTA TCAAACCGGT TGTTCAATTT
2751  CACTGGCAAG GGTGATCAAG ACCCGTCACT AGATAGTGAA TATGCTGCAA
2801  ATTTGAAAGC ATTCAAGTGC ACAGACCTCA ACAAGTTGAA CACCACAAAA
2851  ATTGAGATGG ACCCTGGAAG TCGCAAGACA TTTGATCTTA GCTACTATAG
2901  TCACGTTATT AAGAGAAGGG GTCTATTTGA GTCAGATGCT GCATTATTGA
2951  CTAACTCAGT TACAAAGGCA CAAATCATCC AATTGCTTGA AGGGTCAGTT
3001  GAAAATTTCT TTGCTGAGTT TGCAACCTCC ATCGAGAAAA TGGGAAGAAT
3051  TAATGTGAAG ACAGGGACAG AAGGAGAGAT CAGGAAGCAT TGTGCATTTA
3101  TAAATAGCTA AGAATCTTGT CTTGTTCATG GATGAATCTT GTATCATTTA
3151  TTTTTTGGGG TTTGATTATT TATGCTATGC CATGTTTTTT GATTAGTTAT
3201  GCTATGCCAT GTGGTCTCTG TCTACATACG TGTGATCCTT TATGGTATGG
3251  TTGTTGTATG TGTGTTGGAA TAAGTGGGCT CTTAAGTTAT TCATATTTCC
3301  AACTTTGCTG GTAGATCATG CTCTTGTAAT AAGAACCAGA A
SEQ ID NO:18
```

Figure 14C

```
   1  CAATAATTAT AGTTTGATAG CCTGCTACCA TCAAGGATTG CAATGCAAGC
  51  TTTGGCACCA AAAACAAAAT TACGATGGCT CAACCTCAAC CTTAACTACC
 101  GCATACATTG GTATAACTCA GGCGCAGTTT GGTTTGCTAG TGAAACCACT
 151  AGTGATTTGG TTAGTGCTGA TCAGACTTTG AGTGACTTTT TTATGTCGTG
 201  CCATTTTCAA TTAAATGTCT AAAAATTTTA AGATAATTAA ACAACTTTTT
 251  TATTTTTAAA AAGCTAAAAC ACAAAAGAA ATGAGTACTT TTCTTGTAAA
 301  TTGACAATAA TGGTTTTTTT TATAAAAAAA AAAATAAGTG TCTTACAAAA
 351  GAAAATTATC CAAACATAAC ACTAATATGG CATGGACAAT TGGCCACGAG
 401  GCTGTTGGCC TCAATTTCCG TTGAAAAGCC TAAACTGAAA TATGGCAAGA
 451  GTTTGATCAC AGAAAAAAAT GGTCGGGGTA AAATCAAACT TTCACTTATT
 501  ACATTAGGAC AATAGGAGAA AGACCAAGGA TAATGTCATA ATCAACGAAT
 551  CATAATTATG TATCATGGGG TGGAGGATGA CATCGTGATT TGTGATATTA
 601  CCAACTACTC TTGAAGAGTT TAGACCATGA ACTATAGCT TAAGACTGGA
 651  TTTAGCATGA ATATGTAATT AAATTATTCT GGATCGAGAG TAACATACCA
 701  ATAAAAAAAA AAGAAGAGGA ACATCACAAG CCACAGAAAG CTACCGGAGG
 751  CTTAAAAAGT TTAAGGTTCA TTAGGACGGA GCATAAAGTG GATTGTCTTT
 801  TAGTAATGAG AATGCTTCAA CATTACTACT CTTGATTGAC AGTACTTCTT
 851  AACGAATTGA TTTCTAGGGC CACATTATCT CAAACAATAA TTGATCTCTT
 901  TTATATCTAT AAAAATTCAT TTTCCCCATC TTTGATTTCC ACGGCTAAAA
 951  GCTAAATATC ATCAAAGTAC TCAAATTAGC ATGGCTGTCA TGGTTGCATT
1001  CTTGAATTTG ATCATCATGT TTTCAGTAGT CTCTACAACA GGCAAGTCAC
1051  TGAGCTTAAA CTACTATGCA AAAACATGCC CTAATGTGGA GTTCATTGTT
1101  GCCAAGGCAG TAAAGGATGC CACTGCTAGG AAAAAACTGT TCCAGCAGCA
1151  ATTCTGCGAA TGCACTTCCA TGATTGTTTC GTTCGGGTAA TGCTATTTTG
1201  ACCCCTCCTC CCTCCTTTCC TCTTGACCGT TCCGCCTCAT TTGATGCATC
1251  ATGAAATCAA ATCATATTGT TTTCTTTTTT CCTATACTCT GAAGGGGTG
1301  TGATGCCTCT GTGCTGCTAA ATTCAAAGG AAACAACAAA GCAGAAAAG
```

Figure 15A

```
1351  ACGGGCCACC  AAATGTTTCT  TTGCATGCAT  TCTATGTCAT  TGATGCAGCA
1401  AAGAAAGCAC  TAGAAGCTTC  ATGCCTGGT   GTGGTCTCTT  GTGCTGACAT
1451  CTCTGCTCTG  GCAGCAAGGG  TCGCAGTTTT  TCTGGTAAGA  AAACTTTGAA
1501  AAGTACCAAA  TTTCTCATCA  TTCAGATCCT  AAACTAAACA  ATCATTATGT
1551  CTTCGAGAAT  TGACAAATGC  AGCTAAGGTG  GCTTGTATTT  GGAAGTCTTG
1601  ACTAATTGTA  TAAAATATAT  TCTGCAGTCA  GGAGGACCTA  CATGGGATGT
1651  TCCTAAAGGA  AGAAAGGATG  GTAGAACATC  TAAAGCCAGT  GAAACCAGAC
1701  AATTGCCAGC  ACCAACCTTC  AACTTATCAC  AACTGCGGCA  AGTTTCTCT
1751  CAAAGAGGAC  TGTCAGGGGA  AGACCTGGTA  GCTCTGTCAG  GTAAGCTATT
1801  CCTAAAGTCA  AAACTGCCAA  AACTTGACCA  TTTTTCATTT  ATTCCAATTT
1851  ATATCTGAAT  AGAGTTTAGA  GTTTCTCCTT  TGACTCATAT  GTAGGGGGGC
1901  ACACTTTGGG  TTTCTCTCAC  TGCTCATCTT  TCAAGAACAG  AATCCACAAC
1951  TTCAATGCAA  CACATGATGT  TGACCCTTCA  TTAAATCCAT  CATTTGCAGC
2001  AAAACTGATC  TCAATTTGTC  CACTAAAAAA  TCAGGCAAAA  AATGCAGGCA
2051  CCTCTATGGA  CCCTTCAACA  ACAACTTTTG  ATAATACATA  TTACAGGTTG
2101  ATCCTCCAAC  AGAAAGGCTT  GTTTTCTTCT  GATCAAGTTT  TGCTTGACAA
2151  CCCAGACACT  AAAAATCTGG  TTACAAAGTT  TGCCACCTCA  AAAAAGGCTT
2201  TTTATGAGGC  TTTTGCGAAG  TCCATGATCA  GAATGAGTAG  CTACAATGGT
2251  GGACAGGAGG  TTAGAAGGAC  TGCTGAATGA  tcaattaata  agtcttaaat
2301  caattcaagt  taaattgatg  ttccaaacaa  gttggatcaa  atttcctaga
2351  tgccaagaat  attatgtctt  tttcctctat  taaagaaata  tgtatattta
2401  tctg    SEQ ID NO:19
```

SOYBEAN PEROXYDASE GENE FAMILY AND AN ASSAY FOR DETECTING SOYBEAN PEROXIDASE ACTIVITY

CROSS-REFERENCE TO RELATED APPLICATION

The present application is a continuation-in-part application of application Ser. No. 08/671,320, filed Oct. 27, 1995.

BACKGROUND OF THE INVENTION

The present invention relates to the DNA sequences of the soybean peroxidase, and to the enzymatic assay of peroxidase activity. The invention also relates to the use of soybean peroxidase in immunoassays or oligonucleotide detection. The invention further relates to medical and environmental diagnostics employing anti-soybean peroxidase monoclonal antibody. The invention further relates to diagnostics for oligonucleotides employing anti-soybean peroxidase monoclonal antibody.

Peroxidase is a class of proteins whose primary function is to oxidize a variety of hydrogen donors at the expense of peroxide or molecular oxygen. Areas where peroxidase could have an immediate use are: pulp and paper bleaching; on-site waste destruction; soil remediation; organic synthesis; and diagnostic chemistries.

At present, pulp and paper is bleached using chloride ions as a chemical agent. Soybean peroxidase has several advantages over chlorine bleach: lower cost; environmentally friendly; and hydroxyl ions produced by peroxidase have twice the oxidation power of chlorine ions.

In waste water and soil treatments, peroxidase has advantages since many organic compounds are toxic, inhibitory, or refractory to microbes, and certain organic compounds may result in the production of microbial products that produce toxic or offensive effluent.

The use of oxidation to achieve on-site destruction or detoxification of contaminated water and waste will increase in the future. If carried out to its ultimate stage, oxidation can completely oxidize organic compounds to carbon dioxide, water and salts.

Peroxidase has several uses in organic synthesis. Using peroxidase, researchers synthesized conductive polyaniline that produced only water as a by-product. Peroxidase can also be used in the manufacturing of adhesive and antioxidant intermediates.

Enzymes are now widely used in medical and environmental diagnostics. Horseradish peroxidase has been one of the most satisfactory enzymes but is relatively expensive. It has now been found that soybean peroxidase can be readily harvested from soybean hulls at minimal expense and be substituted for horseradish peroxidase in these diagnostic chemistries.

Several diagnostic chemistries using the enzymatic activity of horseradish peroxidase and polyclonal antibodies have been described in the literature. Horseradish peroxidase has been used for diagnostic determinations of various analytes and has been used as a label in enzyme labeled antibodies used in the determination of immunologically reactive species (i.e., immunoassays). Such determinations can be carried out in solution or in dry analytical elements.

One type of useful assay utilizes enzymatic reactions wherein the analyte, upon contact with the appropriate reagents, reacts with oxygen in the presence of a suitable enzyme to produce hydrogen peroxide in proportion to the concentration of the analyte. A detectable product such as a visible or fluorescent dye is then produced by the reaction of hydrogen peroxide in proportion to the concentration of the analyte in the tested liquids. Peroxidase is generally used in such assays to catalyze the oxidation of the interactive composition by hydrogen peroxide. One example of such an assay is a glucose assay using glucose oxidase. Glucose is oxidized in the presence of oxygen by the enzyme, glucose oxidase, to produce glucolactone and hydrogen peroxide. In the presence of peroxidase, the hydrogen peroxide oxidizes a colorless dye such as tetramethylbenzidine to produce a colored product.

Another type of assay utilizes an immunologically reactive compound such as an antibody. These chemistries can be generally classified into two groups, namely, conjugate or enzyme labeled antibody procedures, and non-conjugate or unlabeled antibody procedures. In the conjugate procedures, the enzyme is covalently linked to the antibody and applied to a sample containing the immobilized antigen to be detected. Thereafter the enzyme substrate, e.g., hydrogen peroxide, and an oxidizable chromogen such as a leuco dye are applied. In the presence of the peroxidase, the peroxide reacts with the chromogen resulting in the production of color. The production of color indicates the presence and in some cases the amount of the antigen. In another method, a competing substance is used to dislodge an antibody enzyme conjugate from an immobilized substrate, leading to an absence of color.

In a method sometimes referred to as the sandwich assay or enzyme linked immunoadsorbent assay (ELISA), a first antibody is bound to a solid support surface and contacted with a fluid sample suspected to contain the antigen to be detected and an enzyme-antibody conjugate. The antigen complexes with the antibody and the conjugate bonds to the antigen. Subsequent introduction of the substrate and chromogen produces a visual indication of the presence of the antigen.

Procedures employing non-conjugated enzymes include the enzyme bridge method and the peroxidase-antiperoxidase method. These methods use an antiperoxidase antibody produced by injecting peroxidase into an animal such as a goat, rabbit or guinea pig. The method does not require chemical conjugation of the antibody to the enzyme but consists of binding the enzyme to the antigen through the antigen-antibody reaction of an immunoglobulin-enzyme bridge. In the enzyme bridge method a secondary antibody acts as an immunologic bridge between the primary antibody against the suspected antigen and the antiperoxidase antibody. The antiperoxidase antibody in turn binds the peroxidase which catalyzes the indicator reaction. In the peroxidase-antiperoxidase method, a complex of the peroxidase and the antiperoxidase antibody is formed. This complex can then be used in the immunologic bridge method.

Though peroxidase genes from different biologic sources have been identified, including other plant peroxidase genes from horseradish, tomato, pea, arabidopsis, peanut and turnip, and bacterial lignin peroxidase gene, there have not been any reports regarding identification of peroxidase genes from soybean.

Soybean coats are abundant and inexpensive, making them an excellent source of peroxidase. Therefore, there is substantial interest in cloning soybean peroxidase genes which will open the possibility of characterization of the expression patterns of individual peroxidase isoforms during normal plant development and genetic and molecular manipulations for increased peroxidase activity.

BRIEF DESCRIPTION OF THE DRAWINGS

FIG. 5 Comparisons of nucleotide sequences of the coding regions of the SEPa1 and SEPa2 genes and the predicted amino acid sequences of SEPa1 (p1) and SEPa2 (p2). Amino acid sequences are shown using the single-letter code. The complete coding and predicted amino acid sequences are given only for SEPa1 (first and third lines, respectively). To emphasize the similarity between the two genes and their products, only those nucleotides in the coding region of SEPa2 and the predicted amino acid that differ from the corresponding ones in SEPa1 and p1 are shown. The dots indicate identity of nucleotides and amino acids. For example, a dot under a nucleotide represents the presence of the same nucleotide that is directly above the dot. The signal peptide is shown in bold italics. The start of the mature proteins begins with the [QLXXXFY] motif at position 1. The cysteine residues in disulfide bridges are shaded. Conserved amino acid areas are outlines.

FIG. 6 Comparisons of the nucleotide sequences of the coding regions of the SEPb1 and SEPb2 genes and the predicted amino acid sequences of SEPb1 (p3) and SEPb2 (p4). Amino acid sequences are shown using the single-letter code. The complete coding and predicted amino acid sequences are given only for SEPb1 (first and third lines, respectively). The dots indicate identity of nucleotides and amino acids. The asterisks indicate the gap of nucleotides and amino acids between SEPb1 and SEPb2, p3 and p3, respectively. The cysteine residues are shaded and the conserved amino acid areas are outlines. For example, a dot under a nucleotide represents the presence of the same nucleotide that is directly above the dot. The signal peptide is shown in bold italics.

FIG. 13 Immunoblot showing transfer of fetuin to immunlon paper in an immunoblotting procedures using fetuin and MM4 antibody.

FIG. 14A–C Genomic DNA sequence for SEPa1 showing with ATG start codon underlined.

FIG. 15A–B Genomic DNA sequence for SEPb1 showing with ATG start codon underlined.

SUMMARY OF THE INVENTION

Figure 1:
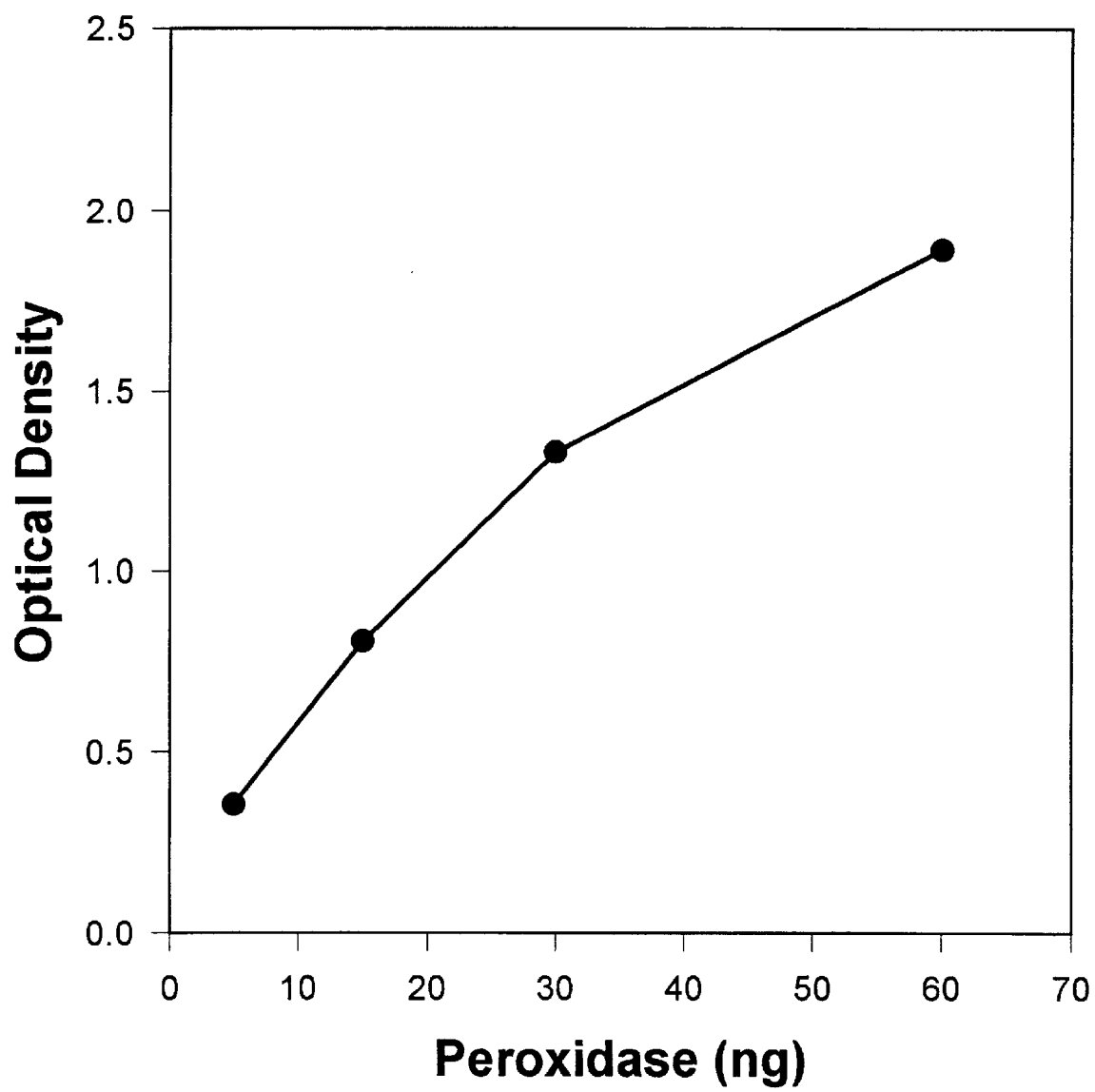
FIG. 1 Average ELISA absorbance (405 nm) of purified peroxidase samples against 1:10 dilution of peroxidase monoclonal antibodies (MAB).

The present invention further involves four DNA sequences representing a soybean peroxidase gene family. These DNA sequences of the present invention encode amino acids that show homology to other plant peroxidase conserved amino acid regions. Outside the conserved regions the sequences show a high degree of divergence from other plant peroxidases. These peroxidases can be used in immunoassays and oligonucleotide assays.

The present invention further relates to genomic sequence of two soybean peroxidases. Each genomic sequence includes the promoter region and the coding region of the particular soybean peroxidase. The soybean peroxidase promoters can be used for preparing transgenic plants, especially transgenic soybeans.

The method of the present invention further relates to a direct method without the secondary enzyme-linked antibody as used in reaction found in ELISA.

The invention also relates to a kit for measuring peroxidase activity outside the laboratory to determine the effect of environment and seed storage on peroxidase activity, and allows direct selection of high peroxidase genotypes in a plant breeding field, grain elevator and processing plant. The kit also allows quantitation and monitoring of peroxidase activity in processes using peroxidase or peroxidase solutions, such as pulp and paper bleaching, on-site waste destruction, soil remediation and organic synthesis.

The present invention also relates to an anti-soybean peroxidase antibody which does not inhibit peroxidase activity which can be used in conventional immunoassays, including but not limited to the following: enzyme capture assay for activity quantification; ELISA for peroxidase concentration; soybean peroxidase capture assay (SPCA) kits for measuring activity outside the lab; ELISA kits for measuring concentration outside the lab; peroxidase-antiperoxidase conjugates; immunohistochemical detection; immunoperoxidase microscopy and immunopurification of peroxidase. The anti-soybean peroxidase antibody is also useful in the immunoassays of the present invention and in assays for oligonucleotides.

The peroxidase-antiperoxidase conjugates of the present invention are useful in the following applications: non-radioactive nucleic acid labeling and detection; conjugating antibody complex in western blot; ELISA reactions; ELISA detection of DNA and RNA; and conjugate to polymerase chain reaction (PCR) products.

Finally, the present invention relates to an immunoasay in which three antibodies are utilized and none of the antibodies are conjugated to an enzyme. The first antibody is specific for the target antigen. The second antibody is an anti-antibody which binds to the first antibody and a third antibody. The third antibody is specific for soybean peroxidase. The third antibody captures soybean peroxidase from a peroxidase solution, eliminating the need to conjugate soybean peroxidase to an antibody and insuring maximal peroxidase activity.

DETAILED DESCRIPTION OF THE INVENTION

The present invention relates to the genomic DNA and promoters of soybean peroxidases and their use as promoters for producing transgenic plants, including transgenic soybeans. The invention also relates to immunoassays or oligouncleotide assays which utilize soybean peroxidase as a marker. The invention further relates to the use of third antibody, an anti-soybean peroxidase antibody, in immunoassays. Soybean peroxidase may be bound to the anti-soybean peroxidase antibody prior to binding of this antibody with the second antibody (anti-antibody) in the assay. Alternatively, the anti-soybean peroxidase antibody is bound to the second antibody (anti-antibody) and then the soybean peroxidase bound by its specific antibody.

In order to provide an understanding of several of the terms used in the specification and claims, the following definitions are provided:

"Operably linked"—The term operably linked refers to a juxtaposition wherein the components so described are in a relationship permitting them to function in their intended manner, i.e., a promoter is operably linked to a coding sequence if the promoter affects its transcription or expression.

"Isolated", "substantially pure" and "substantially homogeneous"—These terms are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95% w/w, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art for purification utilized.

A soybean peroxidase is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Nondestructive"—The term nondestructive refers to the ability of quantitating peroxidase activity without killing the seed, plant or rendering peroxidase non-enzymatically active.

The present invention is directed to a method of quantitating peroxidase activity, a kit for quantitating peroxidase activity, immunological assays, and DNA sequences regulating and representing a soybean peroxidase gene family.

The method of this invention is adaptable to both solution and dry assays and describes the capture of peroxidase by an antibody from a solution. Antibodies are immobilized on a solid support and unbound matrix is blocked with unreactive proteins. Solutions containing peroxidase are incubated with the immobilized antibodies and then removed. Captured peroxidase is then assayed for activity with any substrate, with or without additives, previously used in horseradish peroxidase assays. This invention does not use a secondary enzyme-linked antibody like an ELISA assay.

The method of this invention can also be practiced with a dry analytical element. The kit may be composed of an absorbent carrier material, e.g. a thin sheet of a self-supporting absorbent or bibulous material, such as filter paper or strips, which contains an immobilized antibody. The element can be divided into multiple zones with different compositions of the antibody incorporated into individual zones of the carrier material. Such elements are known as test strips, diagnostic elements, dip sticks, diagnostic agents and the like.

The assay or test kit can be used to quantitate peroxidase activity in plant fluids from macerated tissue with or without exogenous liquid added. Such fluids include, but are not limited to, fluids from leaves, stems, roots, flowers, seeds, seed coats, embryos, hypocotyls, coleoptiles, seed pods and seed buds. It is also possible to assay fluids from a variety of plant species including, but not limited to, soybean, corn, wheat, sorghum and oats.

This invention allows for the selection of high peroxidase plant genotypes in the field of plant breeding. Since minimal amounts of tissue are needed, unlike other methods of assaying peroxidase activity, e.g. Gilliken and Graham, Plant Physiol. 96:214–220 (1991), this invention is non-destructive to the seed or resulting plant. This greatly accelerates the progress of plant breeding for high peroxidase levels. The non-destructive nature allows high peroxidase plant genotypes to be selected and advanced to the next generation. The non-destructive nature of the assay is unique. In addition to the non-destructive nature of the assay, another unique trait of the present invention is the quantitative nature of the assay. Being quantitative, the present invention allows for the ultimate discriminatory assay for the separation of high peroxidase genotypes. Previous assays are not able to separate high peroxidase genotypes, e.g. Buttery & Buzzell, Crop Science 8:722–725 (1968). The ranking of high peroxidase genotypes, based on activity, will allow for the most efficient selection for high peroxidase genotypes. This invention is unique in that it is the only method that is non-destructive to the seed or plant and also is quantitative.

The assay or kit can be used to monitor peroxidase activity in industrial processes and is an identity preserved system to deliver high peroxidase plant material to processors. In an identity preserved system, kits will be used to identify high peroxidase seeds or to monitor activity from the seed company, to the farmer's field, grain elevator, grain truck and finally to the processing facility. The kit also can be used to monitor peroxidase activity in stored peroxidase solutions. In industrial processes that use peroxidase, the kit can be used to monitor peroxidase activity.

In recent years the uses of enzyme-linked immunoassay procedures have become widespread due to their convenience and reduced biohazard risk. Antibodies can be conjugated to enzymes without complete loss of either catalytic or immunological activity. Such enzyme-antibody conjugates can be used in ELISA, histochemical staining reactions and immunoblots (with either substrates that change color, fluoresce or produce light). Luminescing products can be detected using commercially available kits by overlaying the blot with X-ray film. Thus, the invention also can be used to determine antigens using an enzyme-antibody conjugate method. In this embodiment, the enzyme label can be any plant peroxidase that participates in the conversion of a chromogen or luminal to a detectable form. In addition, the present invention improves upon such assays by employing an anti-peroxidase antibody in place of an anti-immunoglobulin antibody-enzyme conjugate. In this instance the anti-peroxidase antibody may be contacted with the peroxidase to bind it prior to the antibody's introduction into the assay. Alternatively, the anti-peroxidase antibody is introduced into the assay and then the peroxidase is added and bound by the anti-peroxidase antibody. The enzyme substrates are then added and assayed according to conventional techniques. An example of this latter method is shown in Example 23.

Theoretically, many different enzymes, such as beta galactosidase and alkaline phosphatase can be used in immunoenzyme conjugates, but in practice, peroxidase is one of the most widely employed. While horseradish peroxidase is the form of choice, other species could be of particular value. It has been discovered that soybean peroxidase possesses properties which offer significant improvement over the standard protocol with horse radish peroxidase. Soybean seed coat peroxidase shows an atypical peroxidase inactivation temperature of 90.5° C. Since soybean peroxidase (SBP) has greater stability, it has the advantage of longer shelf life, and consquently lends itself to the development of clinical kits whose durability provides economic benefits.

Figure 9:
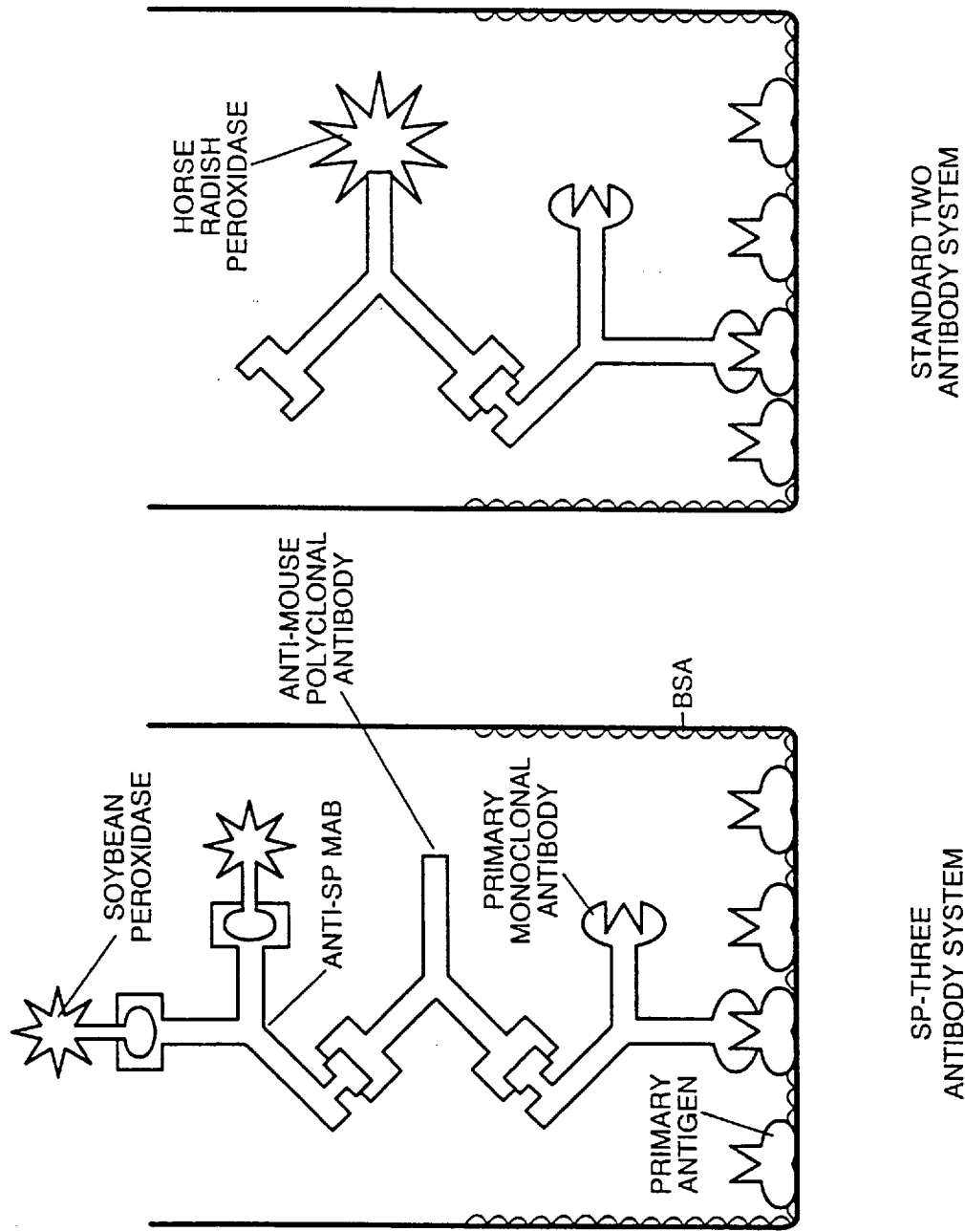
FIG. 9A Illustration of a standard ELISA protocol which employs a specific antibody against a target antigen and an anti-antibody conjugated with an enzyme.
FIG. 9B Illustration of an immunoassay protocol according to the present invention (termed SPAP) which employs a first specific antibody against a target antigen, an anti-antibody against the first antibody and a second antibody against soybean peroxidase and soybean peroxidase.

In addition, in accordance with the present invention, a monoclonal antibody (MAB) against soybean peroxidase was prepared, in order to provide an assay procedure with a higher level of specificity. The standard ELISA protocol employs a specific antibody against a target antigen, which after binding is reacted with a second antibody-enzyme conjugate. See FIG. 9A. The second antibody is generally a polyclonal antibody (PAB) raised in a different species coupled to the enzyme of choice. However, a further aspect of the present invention is the development of an assay which utilizes an addtional step. This addtional step is the binding of an anti-soybean peroxidase MAB to the PAB bound to the first antibody. See FIG. 9B. The anti-soybean peroxidase MAB may have previously been contacted with soybean peroxidase to produce a soybean peroxidase anti-soybean peroxidase antibody complex (SPAP), prior to its introduction into the assay. In this complex the soybean peroxidase is bound to the antibody and not conjugated to it. Alternatively, the anti-soybean peroxidase MAB may be introduced into the assay, and then the soybean peroxidase is added and bound by the antibody. The assay is completed by the addtion of substrate and detection of the product as in conventional assays. This assay provides results which are superior to prior art assays. An example of this assay is set forth in Example 22.

The soybean peroxidase of the present invention can be used to detect oligonucleotides. Classically, specific oligonucleotides are detected by hybridizing with probes that are radiolabeled by the incorporation of radioactive dNTPs. Although sensitive, the value is compromised by the short half life of radioisotopes and the expense and biological hazard associated with usage and disposal. These drawbacks have occasioned the search for alternative methods.

One such method uses a covalent conjugate of an oligonucleotide and an enzyme as shown in U.S. Pat. Nos. 4,962,029, 5,254,469 and 5,272,077, each incorporated herein by reference. Enzymes that can be used include peroxidase, glucose oxidase, alkaline phosphatase and beta-galactosidase. Chemiluminescent substrates are then used to assay for enzymatic activity and luminescing products can be detected by exposing blots to X-ray film. An alternative method uses a biotinylated, oligonucleotide probe that hybridizes to the target oligonucleotide. A strept- or nutra-avidin enzyme conjugate is bound to the biotinylated probe. Chemiluminescent substrates are then used to assay for enzymatic activity and luminescing products can be detected by exposing blots to X-ray film. Problems associated with these methods are lack of sensitivity and high nonspecific binding. A method according to the present invention using an anti-soybean peroxidase MAB to detect target oligonucleotides is illustrated in Example 21. This method can be further modified as described for other assay procedures described herein.

Other uses of the present invention involve the modification of the peroxidase enzyme, the peroxidase gene or bacteria containing the enzyme. The entire gene with its 5'- and 3'-regulatory regions can be manipulated in a variety of ways to provide for expression and enzyme form.

In general, expression can be enhanced by including multiple copies of the peroxidase gene in a transformed bacterial or plant host, by using promoters that initiate transcription at increased levels, or by any known means of enhancing peptide expressions.

A recombinant gene can be constructed that takes advantage of regulatory regions from other genes and the coding region of the peroxidase genes. Alternatively, a recombinant gene can be constructed that takes advantage of the peroxidase regulatory regions and coding regions from other genes.

The invention also relates to soybean peroxidase promoters. The promoters can be used in any conventional manner for plant transformation, particularly for preparing transgenic soybeans.

EXAMPLES

The following examples are provided to further illustrate the present invention and are not intended to limit the invention beyond the limitations set forth in the appended claims.

Example 1

Peroxidase Extraction and Monoclonal Antibody Production

Peroxidase was extracted from circular pieces of seed coat, roughly 3 mm in diameter. Samples from three seeds per replication were placed separately in micro centrifuge tubes containing 1 ml of water, incubated at room temperature for 2 hours and vortexed.

Purified seed coat peroxidase (>95% pure) and seed coat peroxidase solutions with various levels of known pupurogallin (PPU) activity were kindly provided by Enzymol International (Columbus, Ohio).

Seeds of high and low peroxidase cultivars were grown at the Purdue Agronomy Farm at West Lafayette, and a Resnik x Winchester cross was made during the summer of 1993. $F_1$ seeds were grown in Puerto Rico, $F_2$ seeds were grown in West Lafayette and $F_3$ individual seeds were tested for peroxidase activity.

BALB/c mice (Mus musculus) were subcutaneously injected with a total of 0.1 mg purified seed coat peroxidase (>95% pure) kindly provided by Mead Central Research (Chillicothe, Ohio). Fusions with myeloma parent P3/NS1/1-Ag4-1 (NS-1) were done with polyethylene glycol 4000. Hybridomas were selected on hypoxanthine (100 nM), aminopterin (0.4 nM), and thymidine (16 nM) media and clones were obtained using the limited dilution method. Raw ascites solution was collected and used in all procedures. Hybridomas were initially selected on their antibody's ability to bind peroxidase. Hybridomas were subsequently selected on their antibody's ability to bind peroxidase in such a way as to not affect enzymatic ability. We have selected a hybridoma that has been designated A4.

Example 2

Enzyme-linked Immunosorbent Assay (ELISA)

An indirect detection method using an alkaline phosphatase antimouse immunoglobulin and p-nitrophenyl phosphate as the chromogen was used to detect seed coat peroxidase. Raw ascites was diluted 1:10, 1:100, 1:1000, and 1:5000. Quantitation of three wells per replication was done at 405 nm after 45 minutes of development. ELISA detects protein or enzyme concentration but not enzyme activity, so ELISA is not suitable for plant breeding for higher peroxidase activity, or the detection or monitoring of peroxidase activity (FIG. 1)

Example 3

Peroxidase Capture Assay (PCA)

Figure 2:
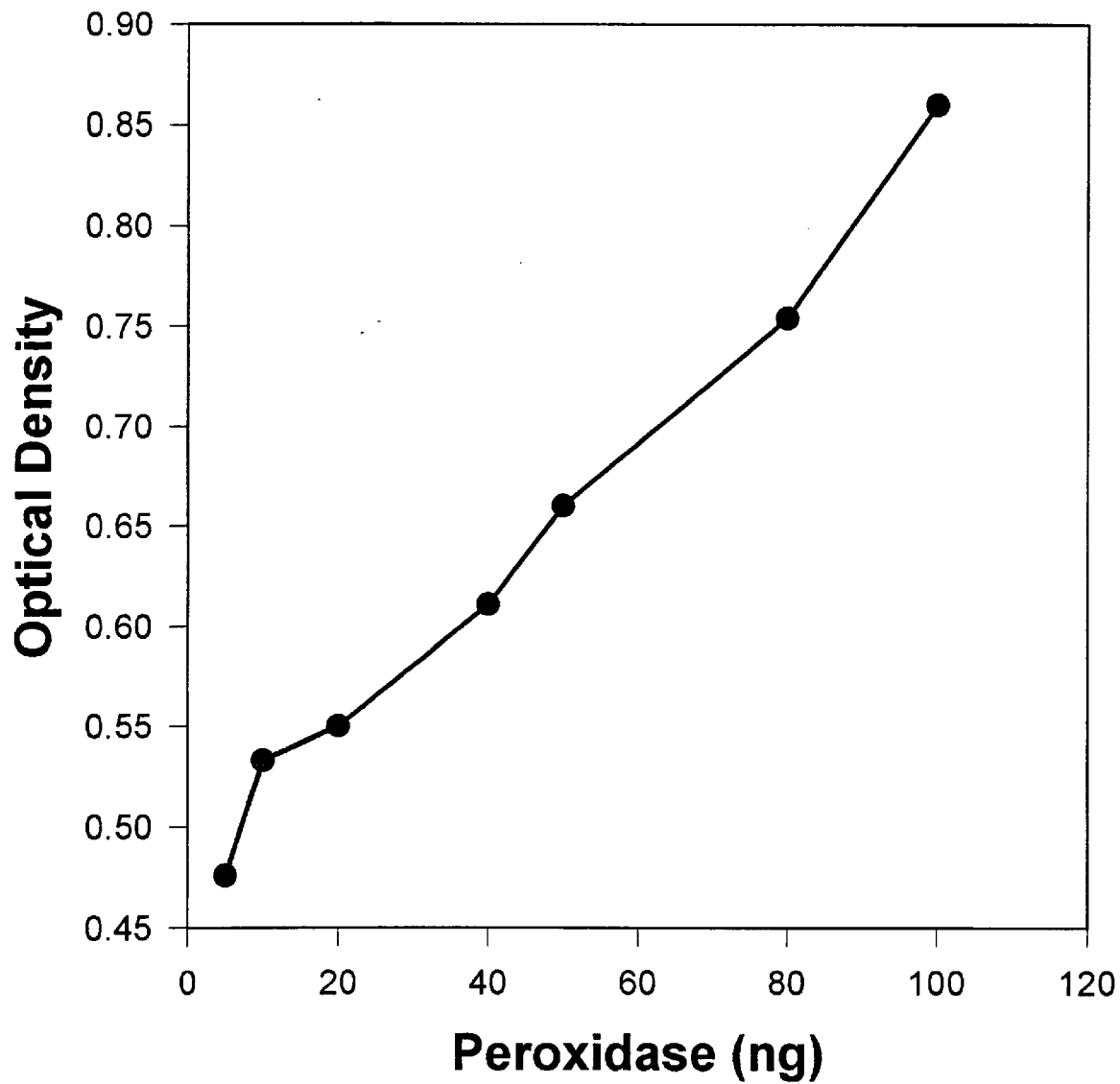
FIG. 2 Average Peroxidase Capture Assay (PCA absorbance (450 nm) of purified peroxidase samples against 1:5000 dilution of peroxidase MAB.

ELISA plate wells were coated with 100 μL of a 1:100, 1:1000, 1:5000, and 1:10,000 dilution of ascites fluid and incubated overnight at 4° C. After incubation, the ascites fluid was removed and 100 μL of 1% (w/v) bovine serum albumin, acting as a blocking agent, was added. After a 1-h incubation at room temperature, wells were washed three times with phosphate-buffered saline (PBS; 137 mM NaCl, 1.47 mM $KH_2PO_4$, 8.10 mM $Na_2HPO_4$, and 2.68 mM KCl, pH 7.4) containing 0.05% (v/v) Tween-20. Peroxidase samples were added to the wells and incubated at room temperature for 1 h. Wells were washed three times with PBS-Tween-20. A soluble, peroxidase chromogenic substrate (100 μL, tetramethylbenzadine) was added to the bound peroxidase. After 30 seconds, the reactions were stopped by the addition of 50 μL of 1N $H_2SO_4$ and three wells per replication were read at 450 nm (FIG. 2).

Example 4

Guaiacol Method

Figure 3:
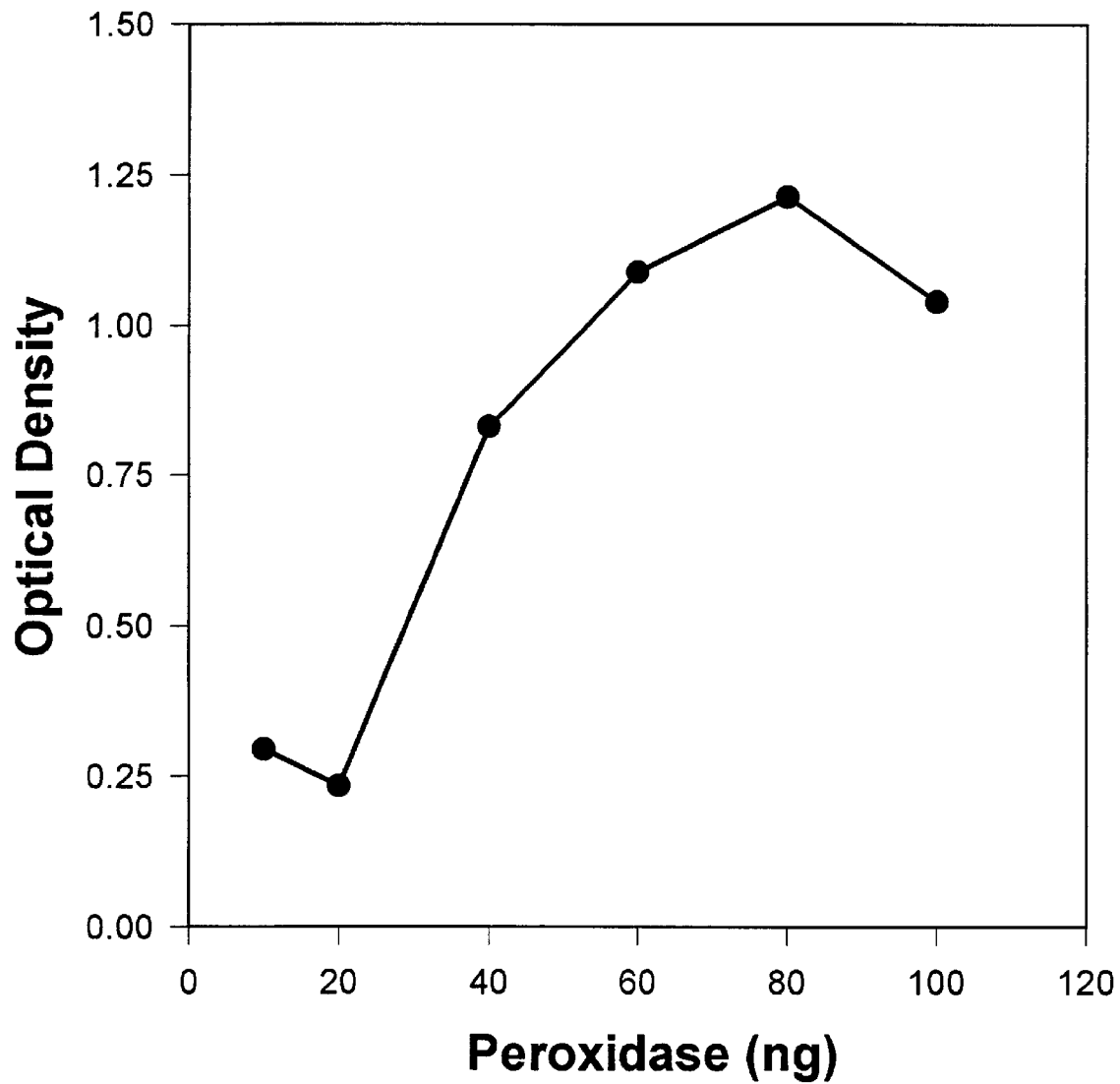
FIG. 3 Average guaiacol absorbance (470 nm) of purified peroxidase.

Purified peroxidase or seed coats were incubated in micro centrifuge tubes containing 1 ml of 0.5% (v/v) guaiacol at room temperature for 10 minutes before the addition of 50 μL of 0.1% (v/v) hydrogen peroxide. After 5 minutes, peroxidase activity was noted, with a brown solution being positive and a clear solution being negative. Peroxidase activity using a guaiacol substrate was also measured at 470 nm as described in Buttery and Buzzell, Crop Science, 8:722–725 (1968). Measurement of known peroxidase solutions, shows this procedure does not give a linear response and is therefore not suitable for plant breeding (FIG. 3).

Example 5

Method Comparison

In the ELISA procedure, we were unable to detect peroxidase with the 1:1000 and 1:5000 dilutions and the 1:100 dilution gave inconsistent results. Using the 1:10 dilution, we were able reproducibly to detect peroxidase. There was no increase in the optical density (OD) beyond 60 ng of peroxidase (FIG. 1).

In the PCA test, the 1:10000 dilution gave inconsistent results. Since the other dilutions gave similar results, the 1:5000 dilution was chosen because it uses the least amount of MAB (FIG. 2). Analysis of variance showed that a linear model explained the data ($R^2=0.99$).

Figure 4:
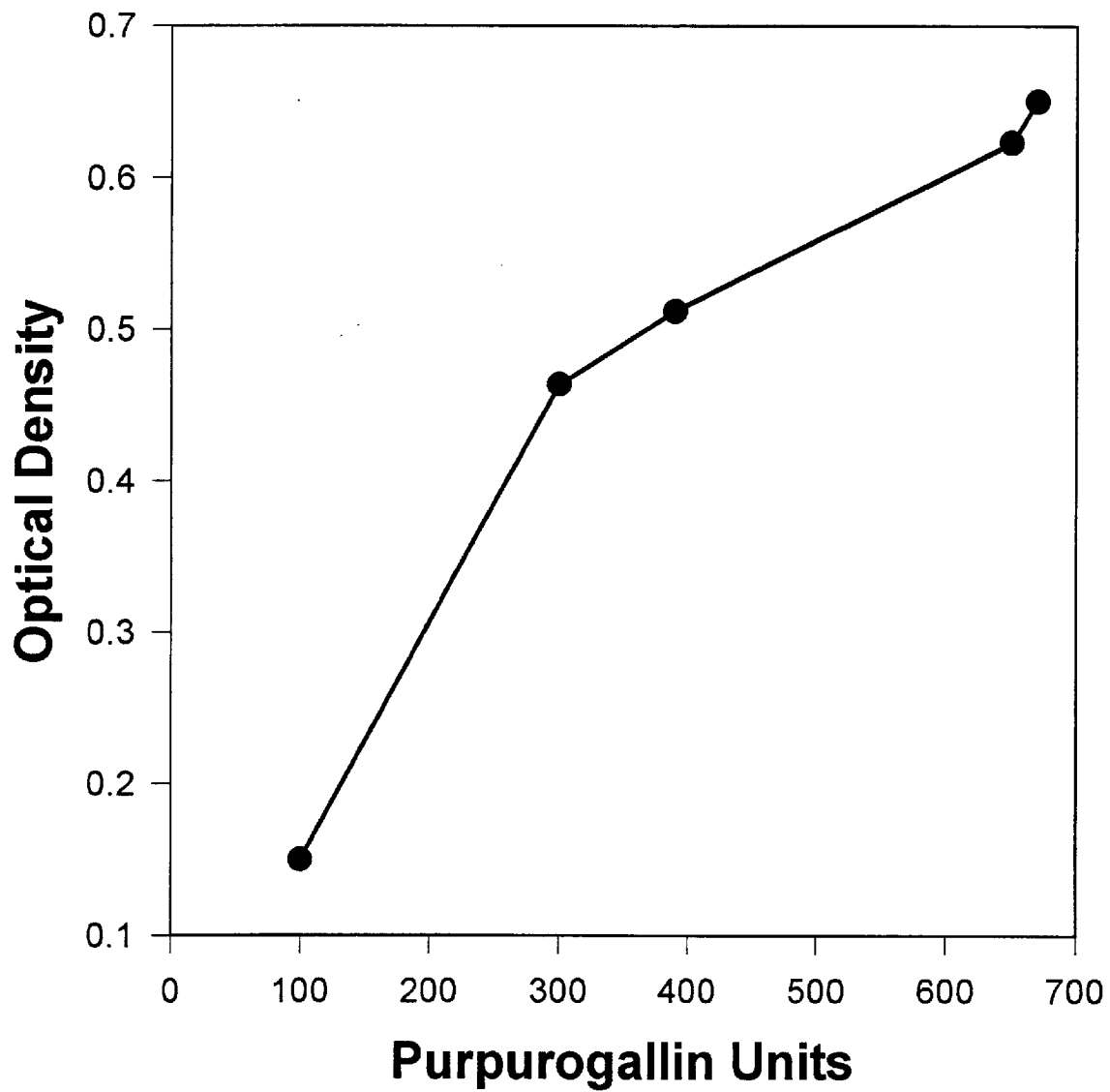
FIG. 4 Average PCA absorbance (450 nm) of peroxidase solutions of known activity against 1:5000 dilution of peroxidase MAB.

Using a guaiacol substrate, peroxidase activity was measured at 470 nm (FIG. 3). Using analysis of variance, a linear model was inadequate to explain the data $R^2=0.77$).
ELISA and PCA Comparison Boiled and nonboiled samples of purified peroxidase, were analyzed using both the ELISA and PCA assays. Presence or absence of peroxidase activities were checked using the guaiacol method (Buttery and Buzzell, 1968).
Analysis of Solutions With Known Peroxidase Activity To determine if PCA could detect differences between samples with different peroxidase activities, samples with 100, 300, 390, 650, 670, 1500, and 2000 PPU/ml were analyzed using PCA (FIG. 4). There was no increase in the OD of the 1500 and 2000 PPU/ml samples over the 670 PPU/ml sample.

There was a major difference between what the PCA and ELISA techniques measured. The ELISA measures peroxidase concentration and not activity; the PCA measures activity not concentration. This was confirmed using the ELISA, PCA, and guaiacol procedures on boiled and nonboiled peroxidase samples. Comparison of the boiled and nonboiled OD of the guaiacol results showed an obvious difference. The guaiacol method showed high peroxidase activity in the nonboiled sample and no peroxidase activity in the boiled sample. The ELISA technique generated OD readings for both the boiled and nonboiled samples. There was a decrease in the ELISA OD between the boiled and nonboiled, which was probably attributable to destruction of the protein during the extended boiling of the sample. By comparison, the PCA OD was 0.0 in the boiled sample and 1.154 in the nonboiled sample. This is consistent with what one would expect looking at the differences between procedures. The ELISA technique used was a two-step indirect method. Conversely, in the PCA technique, peroxidase was captured by the peroxidase monoclonal antibody coating the sample well. There was no secondary enzyme-linked antibody in the reaction. The peroxidase chromogen was added directly to the bound peroxidase, which reacted with the chromogen. Therefore, the PCA technique measures activity and not peroxidase concentration. This is why the boiled sample, which had no activity, had no PCA OD reading. Since the antibody captured peroxidase maintains enzymatic activity, the antibody must bind to an epitope not involved with enzymatic activity.

Solutions with known differences in peroxidase activity were analyzed to confirm the result that PCA gives a quantitative measure of peroxidase activity. Results show that the PCA can detect differences in solutions containing various levels of known peroxidase activity (FIG. 4).

Peroxidase activity also may be measured using guaiacol as a substrate. Comparison of the peroxidase activity curves clearly showed a difference between this method and PCA. There was a linear relationship using PCA, but a linear model was not adequate to describe the relationship using the guaiacol method. A higher order model was needed to explain the guaiacol curve. We believe the PCA technique was superior since the relationship may be explained by a simpler model.

Example 6 cDNA Library Construction

Total RNA was extracted from soybean (Glycine max cul. Resnik) seedbuds 21 days after flowering as previously described (20). Poly(A)-enriched RNA was prepared from total RNA using PolyATract and the cDNA library was constructed in the unidirectional vector Uni-ZAP XR.

Library Screening

A plant peroxidase specific primer (PSP) was generated from a conserved amino acid region (distal heme ligand, HFHDCFV, SEQ ID NO 1) in all plant peroxidases (5'CA(C/T)TT(T/C)CA(C/T)GA(C/T)TG(C/T)TT(C/T)GT3') (SEQ ID NO 2). The probe was generated using the 3'RACE system with soybean seedbud total RNA and PSP as described by the manufacture except that hot-start PCR was performed. The PCR-RACE products were cloned into pCR™II plasmid. DNA from twenty clones was purified and digested with EcoR I, fractionated by electrophoresis on a 1% agarose gel, and blotted on a nylon membrane that was probed with [$\gamma$-$^{32}$p]dATP-end-labeled PSP. A single positive clone was random prime labeled with [$\alpha$-$^{32}$p]dCTP and used for primary screening of the cDNA library ($2.5 \times 10^5$ PFU). Prehybridization was conducted in 6× SSPE, 5× Denhardt's, 0.5% (w/v) SDS, 100 $\mu$g/ml denatured salmon sperm DNA, and 50% formamide at 42° C. for two hours. Hybridizations were performed overnight and the conditions were the same as those in prehybridization except that 1× Denhardt's was used.

PCR using PSP and the T7 vector primer flanking the cloning site was used to purify single phage clones. Phage particles were eluted by incubating primary picks and/or single plagues in 500 $\mu$l of SM buffer (SM: 100 mM NaCl, 10 mM MgSO$_4$, 0.01% w/v gelatin in 50 mM Tris pH 7.5) at room temperature for 2 hours. The PCR cycling parameters were 94° C., 1 minute at 57° C., and 1 minute at 72° C., and followed by a final extension at 72° C. for 5 minutes. PCR reaction conditions were 1× reaction buffer (500 mM KC1, 100 mM Tris-HCl, pH 9.0, 1.0% Triton X-100), 1.5 mM MgCl$_2$, 200 $\mu$M each dNTPs, one unit of Taq DNA polymerase, 1 $\mu$M each primer and 2 $\mu$L of phage particle elution in 50 $\mu$L total.

DNA Sequencing and Sequence Analysis

DNA sequencing of both strands was performed using Sequenase Kit 2.0 (USB) and SK and KS primers (Stratagene). Synthetic primers corresponding to internal sequences of cDNA were made to complete sequencing. Sequence data were analyzed using GCG software (Madison, Wis.).

Example 7

Northern Blot Analysis and RT-PCR

Twenty-five $\mu$g of total RNA from various tissues were fractionated on 1% agarose gel containing formaldehyde, blotted onto nylon membrane, and probed with $^{32}$P labeled probe. Both prehybridization and hybridization conditions were the same as those described in library screening. Sample isolations and hybridizations were replicated twice.

cDNA specific primers designed from 3' untranslated regions of each cDNA and PSP were used in reverse transcript PCR (RT-PCR) to study expression patters. For SEPa1 (SEQ ID NO 10), SEPa2 (SEQ ID NO 12), SEPb1 (SEQ ID NO 14), and SEPb2 (SEQ ID NO 16) the primers were 5'AAATTAACTCAGCTGTGGG3' SEQ ID NO 3, 5'GGAACCCACTTATTCCATCG3' SEQ ID NO 4, 5'CCCAAGACATGCTTGAGAT3' SEQ ID NO 5, and 5'AAGTTCATACTTCTAAC3' SEQ ID NO 6, respectively.

Two $\mu$g of total RNA from different tissues of soybean were used for synthesizing the first strand of CDNA using SUPERSCRIPT™II Rnase H REVERSE TRANSCRIPTASE as suggested by the manufacture (BRL). RT-PCR conditions were the same as those in 3'RACE except that the annealing temperature for SEPb2 was 45° C.

Example 8

Isolation of Soybean Peroxidase cDNAs

The conserved amino acid sequence of plant peroxidases enabled the generation of molecular probe for plant peroxidase genes using 3'RACE. The 3'RACE experiment with PSP and adaptor primer complimentary to the oligo-d(T) end of the cDNA resulted in amplification of a 900-bp DNA fragment (data not shown). Using the fragment as probe, 25 clones were obtained by primary hybridization screening. Eleven positive clones were recovered after two rounds of PCR using PSP and T7 vector primers, and four clones, designated SEPa1, SEPa2, SEPb1, and SEPb2, were further analyzed.

Sequence Analysis of the cDNAs

The nucleotide sequences of the coding regions of SEPa1, SEPa2, SEPb1, and SEPb2, and their predicted amino acid sequences of their protein products, i.e., SEQ ID NOS 11, 13, 15, and 17, are shown in FIGS. 5 and 6. The coding regions of SEPa1 and SEPa2 exhibit 97% amino acid identity, the coding regions of SEPb1 and SEPb2 have 95% amino acid identity, and the coding regions of SEPa1 and SEPb1 share 47% amino acid identity. Comparison of 168 bp, 3' untranslated regions of SEPa1 and SEPa2 revealed 83% homology. The homology between the 187 bp, 3' untranslated regions of SEPb1 and SEPb2 was 75%. There are 6 putative glycosylation sites specified by N-X-T/S at amino acid residues 56, 69, 128, 142, 183 and 214 in SEPa1 and SEPa2, and there are 4 putative glycosylation sites at residues 70, 142, 185 and 195 in SEPb1 and SEPb2, respectively; and SEPa1 and SEPa2 had the [QLXXXFY] SEQ ID NO 7 motif, where X is any amino acid, at the NH$_2$ terminus which is a feature found in most plant peroxidases. No [QLXXXFY] SEQ ID NO 7, motif exists in SEPb1 and SEPb2. Based on predicted amino acid sequences, all four proteins contain a predominantly hydrophobic amino acid signal sequences. Two copies of the putative polyadenylation signals AATAAG, SEQ ID NO 8 are present 39 and 106 bases upstream of the poly (A) signal in SEPa1 and 19 and 75 bases upstream in SEPa2. There is only one copy of the putative polyadenylation signal AATAAA 36 bases upstream of the poly (A) in SEPb1 and 14 bases upstream in SEPb2.

Example 9

Comparisons With Other Plant Peroxidase Sequences

Comparison between the predicted amino acid sequences of soybean peroxidases and some other plant peroxidase sequences. The levels of identity suggests that the clones encode peroxidases. There are three most highly conserved amino acid regions in almost all plant peroxidases. The first is from amino acid residues 33–55 with a predicted disulfide bridge in the middle and a potential heme binding site which belongs to a subdomain of 100% homology: HFHDCFV, SEQ ID NO 9. The second is from amino acid residues 89–105, again with two cysteines that may form disulfide bridges. The third is from amino acid residues 159–170 with a potential heme binding site in the middle. All of the peroxidases studied, except SEPb2, have eight cysteine residues that are located in similar positions in the primary sequences, and two invariable histidine residues (at positions 42 and 167 in soybean peroxidases, FIGS. 5 and 6) are inferred in the active-site structure. The number of glycosylation sites vary greatly according to the isozymes (from 1 in peanut PNC2, 3 and 6 in soybean, to 8 in horseradish).

Differential Expressions of Peroxidase mRNAs

Total RNA from leaf, stem, root, seedbud, and developing seed were probed with a 300 bp Kpn-Tifl fragment from the 3' untranslated region of SEPa1. Data reveals that transcripts of approximately 1400 nucleotides from SEPa1 are present in developing seed and root. Since both the coding regions and the noncoding regions of the four cDNAs are high homologous, RT-PCR experiments were conducted to study the differential expressions of peroxidase mRNA. Data shows the amplification of cDNA synthesized from total RNA of different tissues with PSP and SEPa1-specific primer. To confirm the identity of RT-PCR products, RT-PCR products were transferred to nylon membrane and hybridized with SEPa1 from which SEPa1-specific primer was designed. Based on the results of RT-PCR with cDNA-specific primers, transcripts from SEPa2 were also detected in root and developing seed, and transcripts from SEPb1 and SEPb2 were detected in root, stem, leaf, and seedpod.

Example 10

Peroxidase Cloning

Our results demonstrate that PCR coupled with one round of conventional plaque lift hybridization was effective and rapid in both characterizing and screening of cDNA libraries provided that sequence information is available. This method would a be especially useful when high density plating is used to obtain low abundance clones. Using PSP coupled with a vector primer, one can easily find the primary picks that are true positive clones. By replating the primary picks at low density, individual positive clones can be easily recovered by a second round of PCR with the same pair of primers. Directly using phage particle elution as template in PCR reactions without further precipitation was easily accomplished. The technique amplified a single, distinct product band from as few as $1\times10^6$ phage particles that corresponds to ~0.1 ng of DNA, or as many as $1\times10^8$ phage particles have been used under the same amplification conditions with no detectable loss of specificity. Another advantage of this method is the size of the insert of positive clones can be predicted. A gene-specific primer coupled with vector primer also can be used to reveal the presence of genes of interest in a library prior to screening due to the high sensitivity of PCR. Failure to amplify any product of interest from the library may indicate that full-length cDNA of interest is not likely to be present in the library. In such case, unproductive screening can be avoided.

The predicted amino acid sequences of the four cDNA exhibit homology to other plant peroxidases indicating that the clones encode peroxidase. Each enzyme, except SEPb2, has eight cysteines in nearly identical positions in the primary sequences. Similar cysteines in horseradish and turnip enzymes had been shown to be involved in intramolecular disulfide linkages. By analogy with horseradish and turnip sequences four intrachain disulfide linkages can be predicted in the soybean isoperoxidases SEPa1 and SEPa2 (cysteine pairs between residues 11/89, 44/49/, 95/298 and 174/207).

There are three highly conserved amino acid sequences in all plant peroxidases. The first and the third contain the distal and proximal histidine residues concerned with binding the heme group. The first critical histidine ligand in SEPa1, SEPa2, SEPb1, and SEPb2 occurs at amino acid 42 in the mature proteins, thought to act in acid/base catalysis, and the second at 167 thought to bind the 5th ligand of heme iron. His-42 and His-167 are almost at identical positions in all plant peroxidases.

Plant peroxidases differ greatly in the number and the position of putative glycosylation sites and the heterogeneity of glycosylation indicated that peroxidases exist in differently glycosylated forms or glycoforms. Variability in N-linked oligosaccharide chain location may be adaptively important for fine tuning catalytic properties of the functional enzyme molecule. However, a glycosylation site at residue 183 in SEPa1 and SEPa2 (185 in SEPb1 and SEPb2) is common to most plant peroxidases.

It is predicted from the cDNA sequences that all four proteins are initially synthesized as preproteins with predominantly hydrophobic amino acid signal sequences, suggesting that the mature proteins could be secreted through cell membranes. The hydrophobic residues in the signal peptides are of great importance and signal peptides are believed to function primarily by interacting favorably with the nonopolar interior of the membrane, entering and spanning it. All cloned plant peroxidases so far have a signal peptide and are therefor targeted to the secondary pathway. This was confirmed by biochemical studies of tobacco peroxidases localizing the peroxidases with pl 7.2–7.5 to the vacuoles and acidic peroxidases to the cell walls. It was reported that a C-terminal propeptide of 15 residues was necessary for proper sorting of barley lectin to vacuoles and that the vacuolar protein had this signal removed. Comparison of horseradish C protein and the cDNA derived sequences showed that 15 residues were removed at the C-terminus. The deduced amino acid sequences of soybean peroxidases showed no C-terminal extension present in peroxidases targeted to the vacuole.

Soybean peroxidases SEPb1 and SEPb2 may represent a new family of plant peroxidases and, perhaps, a new, unique biological function, as it is less than 50% amino acid identical to other known peroxidases. Cluster analysis of 2 plant peroxidases showed that SEPb1 and SEPb2 form a distinct group. SEPa1 and SEPa2 show about 67% amino acid identity to tomato anionic peroxidases tap1 and tap2. Using tap1 or tap2 promoter/GUS fusions, the indution of the peroxidase genes by wounding and pathogen attack has been reported, (Mohan, et al., Plant Molecular Biology 21:341–354, 1993). This suggests a role of these peroxidase genes in wound healing process and in the plant defense response. A root-specific peroxidase gene has been described in *Nicotiana sylvestris* and its expression was initially linked to the initiation of the cell cycle of in vitro cultured protoplasts. Acidic tobacco peroxidase TOP A is a constitutive, cell wall bound peroxidase most abundant in root and stem and thought to participate in secondary cell wall thickening. Over-expression of TOP A in transgenic tobacco gave rise to light-dependent wilting. A powdery mildew induced peroxidase pPOX381 of wheat leaves is about 90% identical to a constitutive wheat root peroxidase. The pPOX381 is 57% identical to TP 7, a highly basic peroxidase of the evolutionarily remote turnip, suggesting that these peroxidases might share common functional roles. These very different characteristics of plant peroxidase families may indicate that peroxidases have evolved to participate in very different biological functions.

Our results showed that RT-PCR with gene-specific primers is an effective and sensitive way to study expression of highly homologous genes. The result of RT-PCR was the same as that of Northern blotting, but RT-PCR in which 2 µg of total RNA was used is more sensitive than Northern blot in which 25 µg of total RNA was used in detection of gene expression. The expression patterns of the genes obtained from both northern analysis and RT-PCR indicates differential expressions of various genes. In studies of other plants, there was evidence of differential expression of peroxidase genes. It is not apparent why some organisms have a relatively large number of expressed peroxidase genes. One possibility is that the different encoded proteins have different functions. However, different isoforms can be produced by post-translational modification, suggesting that different genes might not be necessary to provide different functions. A second possibility is that multiple genes could allow for greater regulatory flexibility. Some genes may be expressed in specific organs or at specific stages, and the expression of the genes may be determined by different signals. Regulations studies of the different peroxidase genes and the specific functions of their products are under way.

Example 11

Detection of Soybean Cyst Nematode Feeding

Soybean cyst nematode (SCN) is a major pest of soybean, which decreases yield by feeding on roots. Seedlings from 4 SCN resistant and 2 susceptible cultivars were challenged with 3000 SCN juveniles. Control seedlings were not challenged with SCN. Samples were collected at 0, 1, 2, 3 and 4 weeks and peroxidase activity assayed according to example 3. There was no increase in peroxidase activity at weeks 1 and 2. There was increased peroxidase activity in all cultivars at week 3 (range 3 to 89%). At week 4 the increase in activity ranged from 4 to 41%. By week 5 there was no increased peroxidase activity in the SCN challenged samples. Samples were taken from root tissue.

Example 12

Quantitation of Peroxidase Activity in Stored Seeds

Seeds from high peroxidase soybean cultivars were stored under various conditions to determine factors that affect peroxidase activity. Two replicates of seed lots were stored at 10° C., 20° C., 30° C., 40° C. and warehouse conditions. Seed were equilibrated to moistures of 9 and 13%. Samples were drawn monthly except for 40° C., which was drawn weekly. Peroxidase activity was determined according to Example 3. Results show that the greater the temperature, the greater the decrease in peroxidase activity.

Example 13

Immunopurification of Peroxidase

Peroxidase was purified from plant fluid and solutions by immunoprecipitation. Solutions containing peroxidase were mixed with said antibody. Protein A-Sepharose was added to the peroxidase/antibody mixture and incubated for one hour at 4° C. The tertiary protein A—peroxidase antibody complex was collected by centrifugation and washed three times. The resuspended sepharose beads were incubated at 4° C. for 20 minutes. After the last wash, 30 µl of gel-loading buffer was added to the beads. Samples were heated to 100° C. for 3 minutes and the protein A-sepharose was removed by centrifugation. Purified proteins were separated on a nondenaturing acrylamide gel and visualized by histochemical staining using tetramethylbenzadine as a chromogen. Results shaved a single peroxidase band on the gel.

Example 14

Crop and Cultivar Screening

Figure 7:
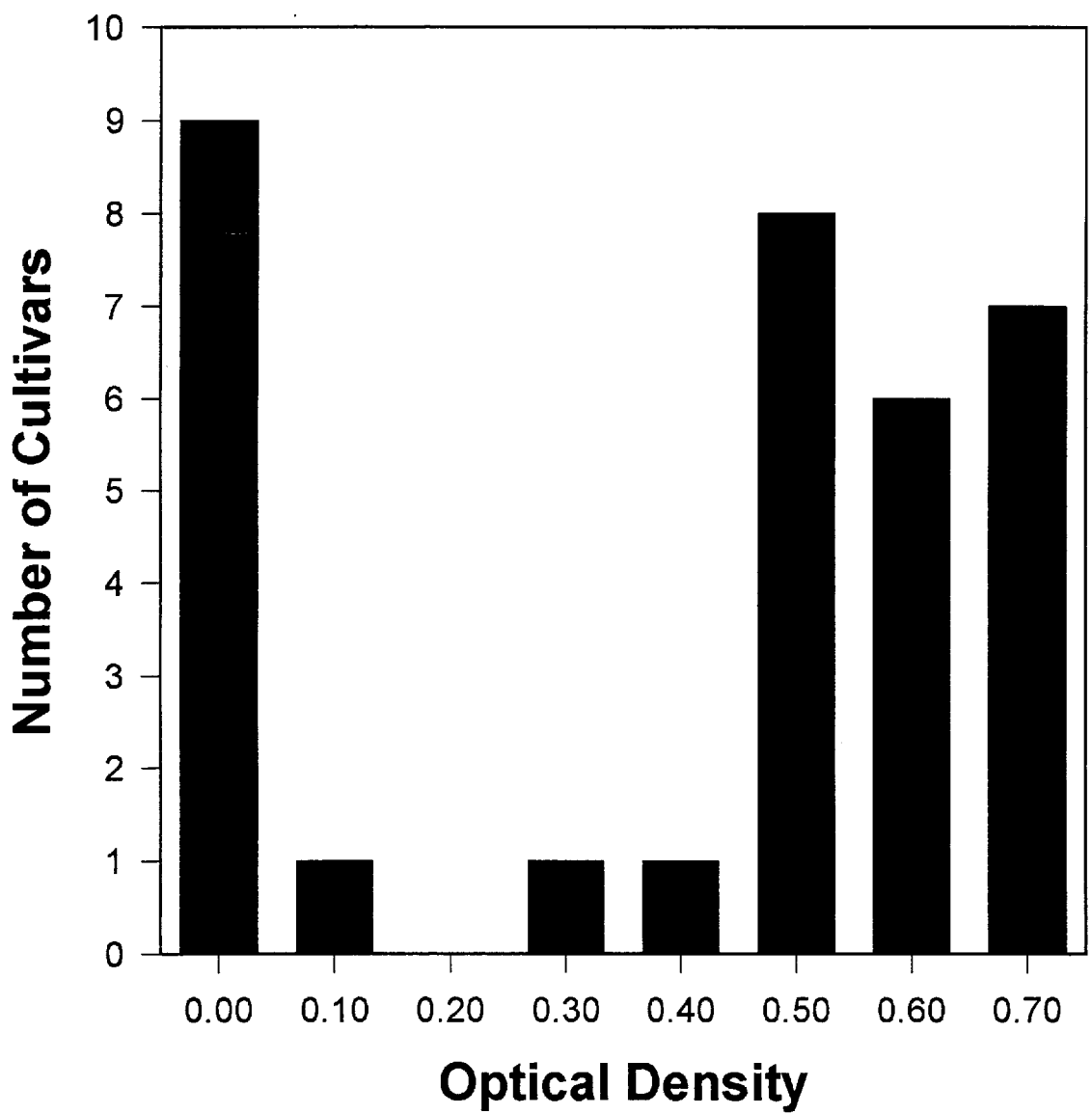
FIG. 7 Histogram of average SPCA absorbance of cultivars.
Figure 8:
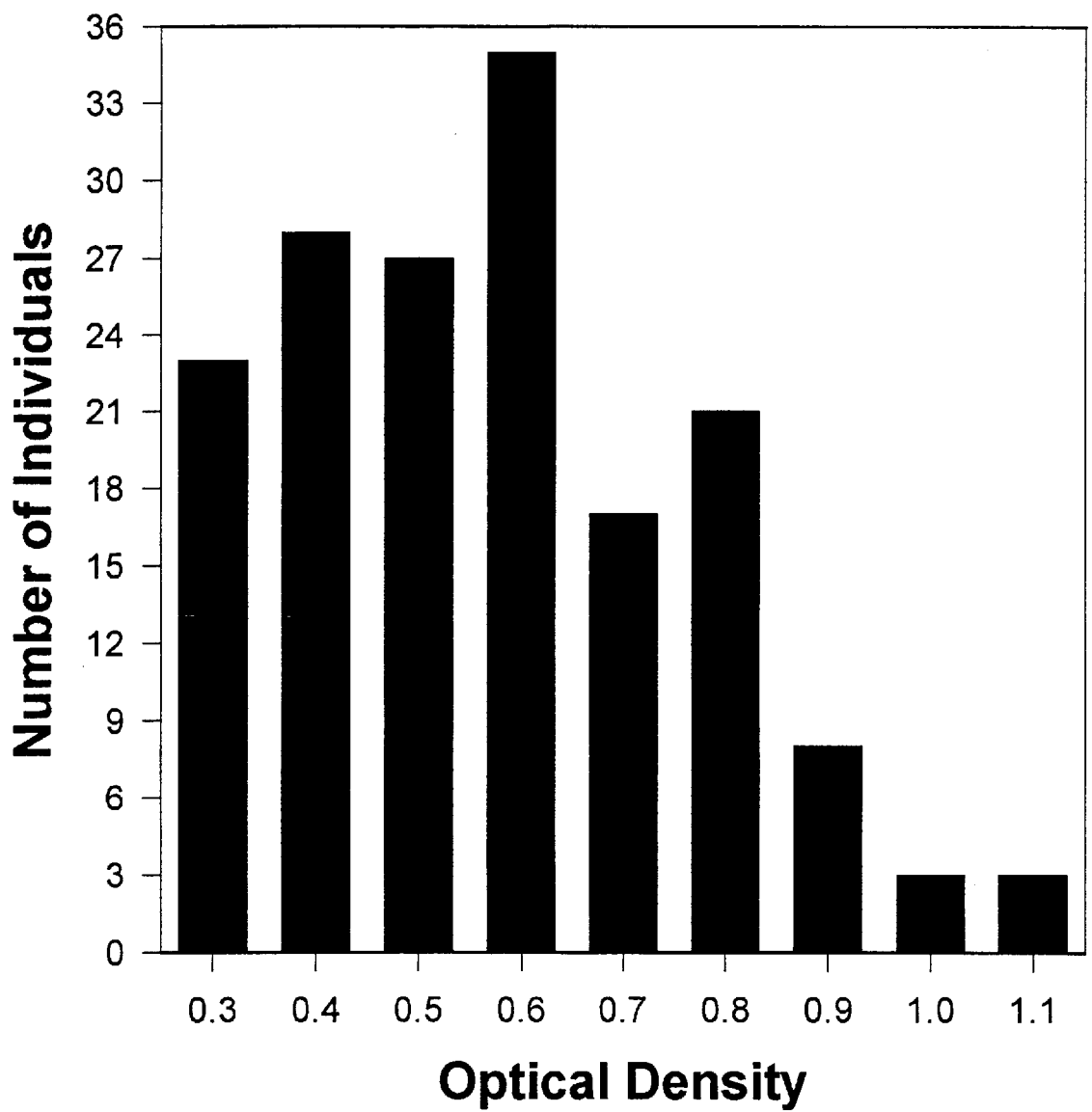
FIG. 8 Histogram of average absorbance of genotypes within an $F_3$ segregating population. Optical density values were 0.777 for Resnik and 0.502 for Winchester.

The use of said antibody is not limited to soybean. In soybeans though, 306 plant introductions from USDA and 33 cultivars were screened for peroxidase activity (FIG. 7). The invention is also useful for screening segregating populations as in a plant breeding program. The means from three replications of the high-peroxidase cultivars used as parents in the cross, Winchester and Resnik, were 0.502±0.038 and 0.777±0.082 respectively. PCA detected differences in a segregating population (FIG. 8). One hundred fifteen progeny from a cross of two high peroxidase cultivars were screened for peroxidase activity. Genotypes with peroxidase activity higher than both parents were identified. The said invention also detected differences in peroxidase activity between 9 sorghum, 5 wheat, 5 corn and 2 oat cultivars.

Analysis of the segregating population showed that PCA can detect differences in peroxidase activity and genotypes with activity greater than the highest parent were identified. PCA will therefore be useful in the introgression of high peroxidase activity into breeding lines. The PCA technique uses the same equipment as the ELISA technique and large scale screening will therefore be routinely available. Results show that peroxidase can be easily extracted from seed coats without destroying the seed. Besides being a valuable procedure for screening cultivars for high peroxidase activity, this technique also will permit investigations of the effect environment and seed storage have on peroxidase activity.

Example 15

Increased Peroxidase Activity in Plants

Peroxidase activity can be increased through plant breeding as described in Example 14. Another method is through plant transformation. Duplicate copies of the gene may be incorporated into plants. Another manifestation is the transformation of altered or mutant copies of the gene. DNA sequences may be altered by means of in vitro mutagenesis and alteration of the regulatory regions, promoter, 5'- and 3' untranslated regions, coding regions or termination sequences may increase expression of the peroxidase gene. Transformation and production of peroxidase is not limited to soybeans and may be accomplished in plants that are transformable.

Example 16

Production of Peroxidase in Bacteria

A single recombinant colony was incubated overnight at 37° C. in 3 ml of LB medium containing 100 µg/ml ampicillin. One ml of culture was used to inoculate 50 ml of fresh LB containing ampicillin and allowed to grow to an $OD_{600}$=0.5. IPTG was added to a final concentration of 0.5 mM and incubated for an additional 4 hours. Two hundred µl of the culture was pelleted by centrifugation and resuspended in 100 μl of TE. Bacteria was homogenized for 45 seconds with an acetal pestle. The homogenate was centrifuged and 50 μl of the supernatant was analyzed on both an acrylamide gel and the invention as stated in example 3. Functional peroxidase was isolated from bacterial cultures.

Example 17

Genomic Library Construction and Screening

Soybean nuclear DNA was restriction digested with Xho I and ligated into Xho I digested EMBL3 SP6/T7 lambda arms (Stratagene). The genomic library was screened by one round of lift hybridization and positive clones were purified by two rounds of PCR screening. For lift hybridizations, $5 \times 10^5$ plaques were plated and hybridized with a mixture of $^{32}$P-dCTP randomly labeled cDNAs from example 6. Two rounds of PCR screening were performed on 14 clones to purify positive clones. PCR primers designed from 5' and 3' ultratranslated regions of the 4 cDNAs (examples 6 and 8) were used in PCR screening. Four genomic clones were recovered.

Example 18

Production of Transgenes in Soybean

Transformed plants comprising a recombinant DNA sequence under modified or unmodified transcriptional and translational control of the peroxidase promoter and containing the hydrophobic leader sequence and a sequence encoding a protein or polypeptide will be expressed in the seed coat. Expressed transgenes may be antigenic and act as an animal or human vaccine. Transgenes also may be enzymes or nonenzymatic proteins.

Example 19

Solid-Phase Peroxidase

Peroxidase captured by the said antibody still maintains oxidative activity, therefore antibody bound peroxidase can be immobilized on a solid state matrix (e.g. polystyrene, sepharose column). In oxidative reactions where peroxidase is being used, reagents may be passed through or over immobilized peroxidase and product or modified reagents collected.

Example 20

Non-radioactive Detection of Nucleic Acids

Peroxidase can be covalently conjugated to oligonucleotides. This conjugate can be used as a probe in hybridization assays and in polymerase chain reaction procedures as described in U.S. Pat. Nos. 5,254,469 and 5,272,077. The said antibody can be used to purify the oligonucleotide peroxidase conjugate (Example 13). Said antibody may be conjugated with enzyme, such as peroxidase, glucose oxidase, alkaline phosphatase and beta-galactosidase and used in the detection of nucleic acid providing an appropriate chromogen, fluorogen, chemiluminescent or substrate is provided.

Example 21

Oligonucleotide Detection Using Soybean Peroxidase

A method using an anti-peroxidase MAB to detect target oligonucleotides is illustrated in this example. Anonymous human DNA was restriction digested with HindIII and separated on a 0.7% agarose gel. DNA was transferred to nylon membranes by standard protocols. Oligonucleotide probes were synthesized by polymerase chain reaction from pV47-2 using M13 primers. Biotinylated dCTPs were incorporated into the probe by random priming. Biotinylated probe was hybridized to target DNA using standard procedures. Hybridized blots were incubated with nutraavidin conjugated polyclonal antibodies (PAB) against mouse immunoglobulins. An anti-peroxidase MAB having been previously contacted with soybean peroxidase was then bound to the antimouse PAB and the blot incubated in chemilumescing substrate. Luminescing products were detected by exposure to x-ray film. Alteratively, the anti-preoxidase MAB is bound to the antimouse PAB and then soybean peroxidase is bound to the anti-peroxidase MAB. The detection of bound soybean peroxidase is detected as described.

Example 22

Immunoassay Using Three Antibody System and Soybean Peroxidase

This example illustrates the three antibody system with the use of soybean peroxidase and the superior properties of the assay system. The three antibody system is an immunoassay procedure that takes advantage of triple layer sandwich with a MAB directed against soybean peroxidase. The anti-soybean peroxidase is used to bind soybean peroxidase, rather than conjugating the enzyme to an anti-antibody.

The antibodies used in the validation of the present procedure (SBP system) were MM4, a MAB described by Tong et al. (Blood 69:238, 1987) and developed as an antibody against myeloma cells. The MM4 antibody reacts against fetuin, a widely distributed fetal protein. In preliminary experiments, it was found that the specificity of the MM4 MAB for fetuin is quite strong, leading to the conclusion that MM4 MAB is a useful reagent for the characterization of the SBP system. The antibody against soybean lipoxygenase (Yabuuchi et al., Crop Science 22:333, 1982) is a dioxygenase that is present in soybean seeds.

Fetal bovine serum, a complex mixture consisting of many proteins, was used as a crude fetuin preparation. Purified fetuin was obtained commercially (all chemicals were obtained from Sigma, St. Louis, Mo., unless otherwise indicated). Alpha feto-protein was purified from a human hepatoma cell line using the OM 3-1.1 MAB.

The ELISA procedure was carried out using standard methodology (Chaffin, et al., Infect. Immun. 56:302, 1988; Morrow, et al., In: Colloidal Gold: Principles, Methods and Applications, III, M. Hayat (Ed.) Academic Press, New York, pp.31–57, 1991). Briefly, Nunc Maxisorp Immunoplates (Fisher Scientific, Houston, Tex.) were coated with antigens (concentrations as indicated) and incubated for 24 hours at 4° C. They were blocked with 1% BSA in PBS and incubated for 24 hours at 4° C. They were rinsed thoroughly in PBS plus Tween 20 (0.1%) and incubated with the appropriate antibodies, in each case for 24 hours at 4° C.

Between each incubation the plates were rinsed thoroughly five times in PBS plus Tween. The plates were developed using ortho-phenylene diamine and hydrogen peroxide dissolved in citric acid buffer (pH 4.9), and developed in the dark for 15 minuets until the reaction was terminated through addition of 50 μl of 1N $H_2SO_4$. The plates were read on an automated ELISA plate reader at an OD of 450 nm.

Immunoblotting was performed according to standard protocols (Xiang, et al., J. Immunol. Meth. 168:275, 1994: Morrow, et al., supra; Hirasawa, et al., Biochem. Biophys. Acta 977:150, 1989; Hirasawa, et al., Biochem. Biophys. Acta 944:229, 1989). Briefly, proteins were separated by PAGE according to Laemmli (Nature 227:680, 1970) using precast gradient minigels (BioRad) and transferred by immunoblotting onto Immulon (Millipore; New Bedford, Mass.) paper in a BioRad transblot transfer cell according to the manufacturer's instructions. Antibody reactive proteins were detected with an ECL Western blotting detection kit (Amersham) according to the manufacturers's instructions. The three antibodies were each reacted with the paper by diluting them and incubating each with agitation in the cold for 60 minutes. Between each step the blots were rinsed thoroughly in PBS plus Tween. The blot was then incubated with the ECL reagents for one minute, wrapped in plastic wrap, and pressed against Kodak Xomat LS film for several seconds (times determined empirically).

Figure 10:
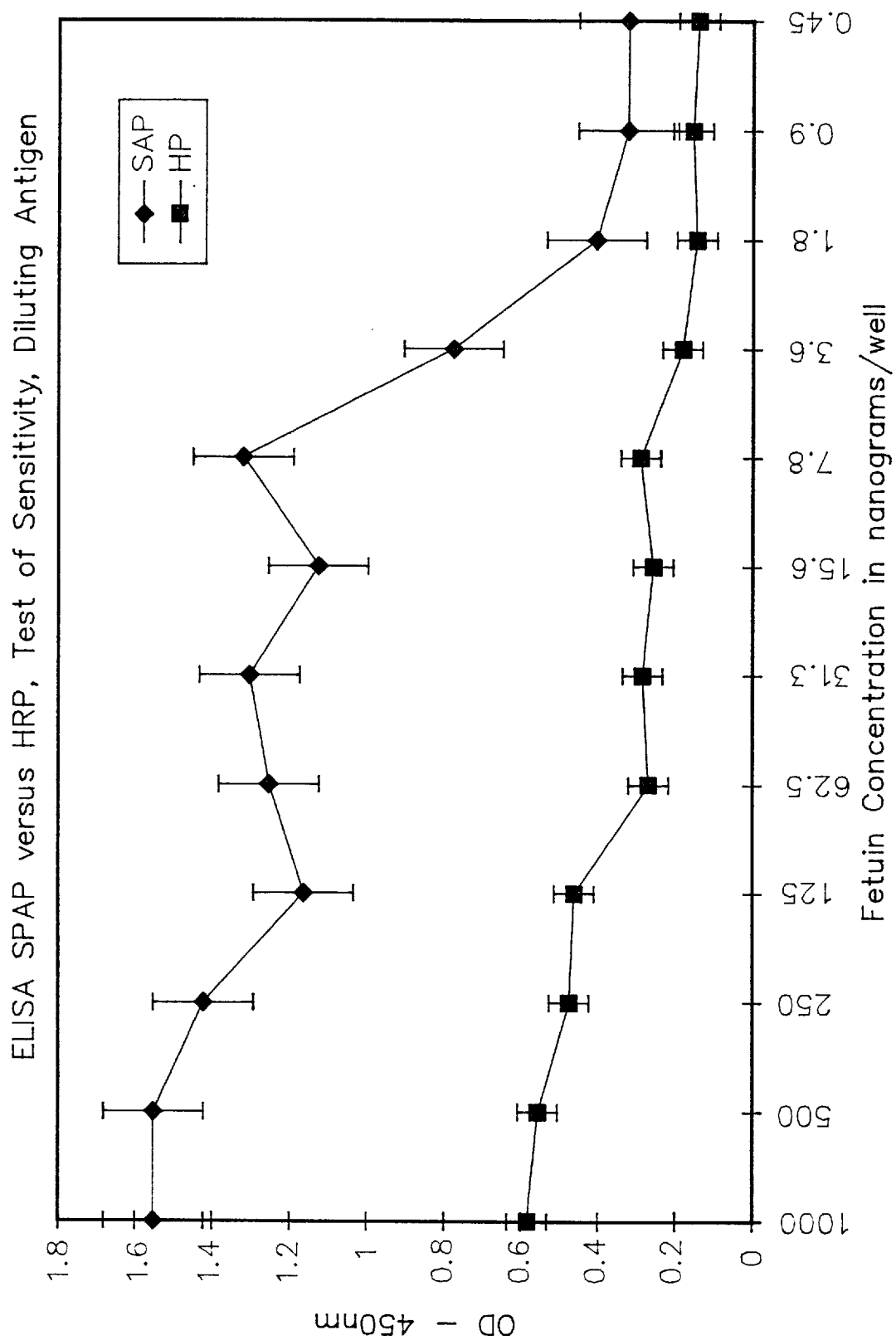
FIG. 10 ELISA results comparing SPAP three antibody system with the horse radish peroxidase (HRP) two antibody system using purified fetuin (antigen) and MM4 MAB. OD readings are averages of four replicates.

The three antibody assay (SPAP) of the present invention was evaluated using ELISA procedures, and comparing the results with a standard two antibody protocol. Dilutions of the antigen, using the fetuin-MM4 system were first tested. As indicated in FIG. 10, as little as 1.8 ng of fetuin antigen with SPAP system was detected, whereas the limit of sensitivity of the standard HRP two antibody method was only around 62.5 ng. Thus, the SPAP system was more than an order of magnitude more sensitive. When the MAB MM4 was omitted or when the second antibody was omitted, there was no interfering activity.

Figure 11A:
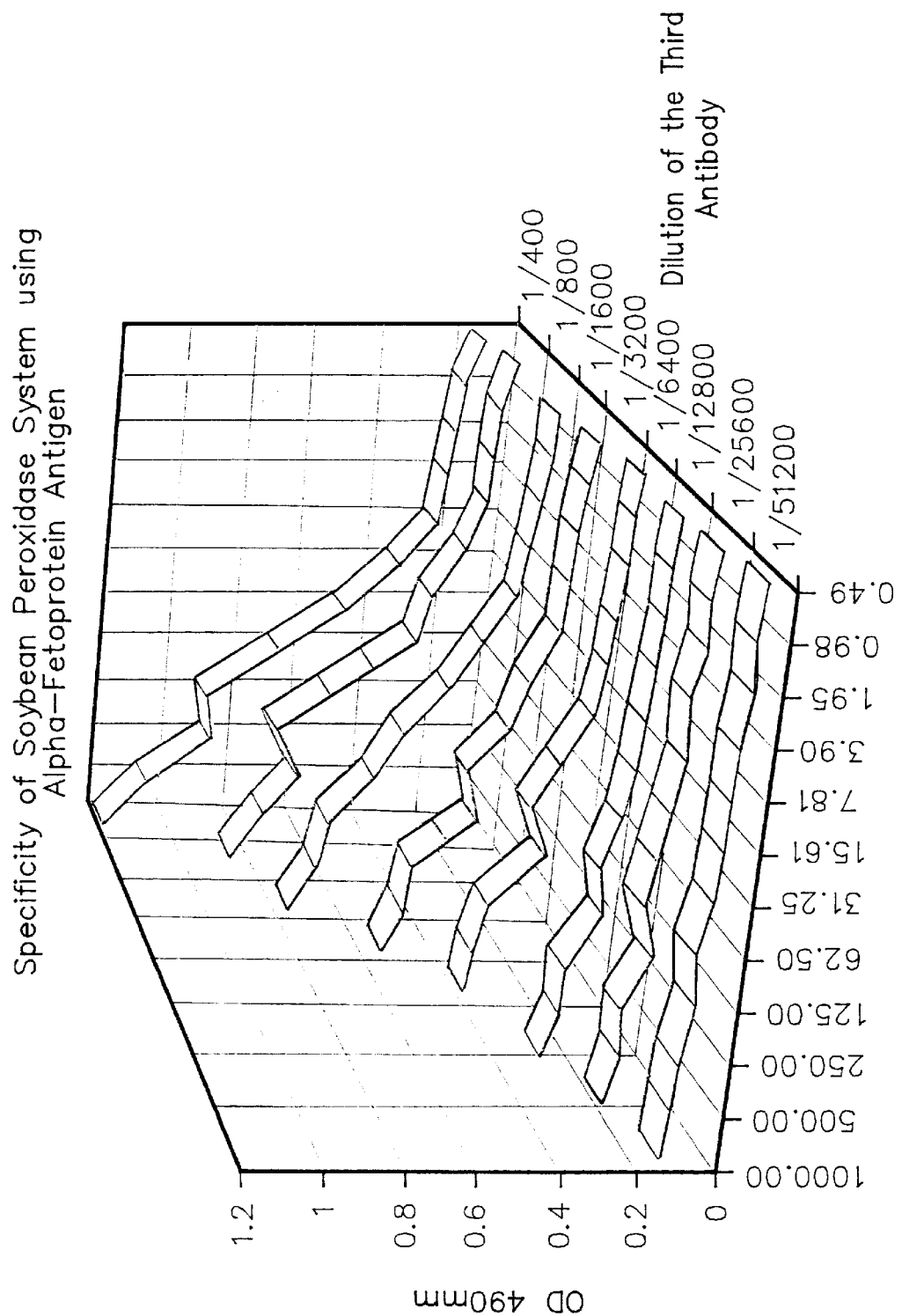
FIG. 11A Three dimensional plot demonstrating effect of varying antigen and third antibody in SPAP system. The range of antigen concentrations was 0.49 to 1000 nanograms/well.
Figure 11B:
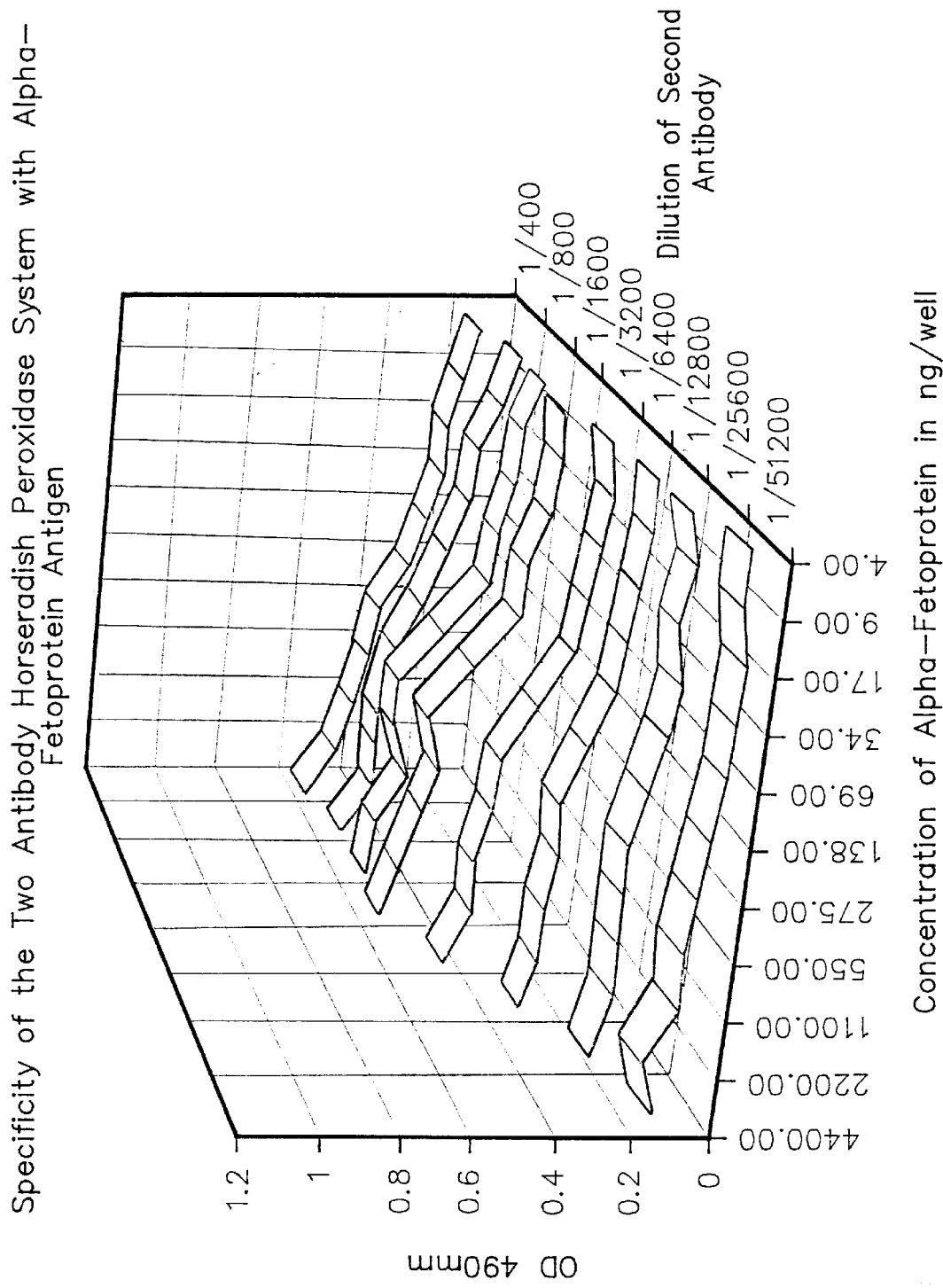
FIG. 11B Three dimensional plot demonstrating effect of varying antigen and second antibody in theconventional two antibody system using conjugated horse radish peroxidase (HRP). The range of antigen concentrations was 4–4400 nanograms/well.

In order to eliminate the possibility that the superior results obtained in the first experiments were a feature of the primary antibody, the two systems were investigated, using alpha-fetoprotein and the OM3 antibody, a totally unrelated system. When the HRP and SPAP systems were compared (FIGS. 11B and 11A, respectively), the SPAP system was superior, giving a stronger signal at every comparable concentrations of antigen than the HRP (FIGS. 11A and 11B).

Figure 12:
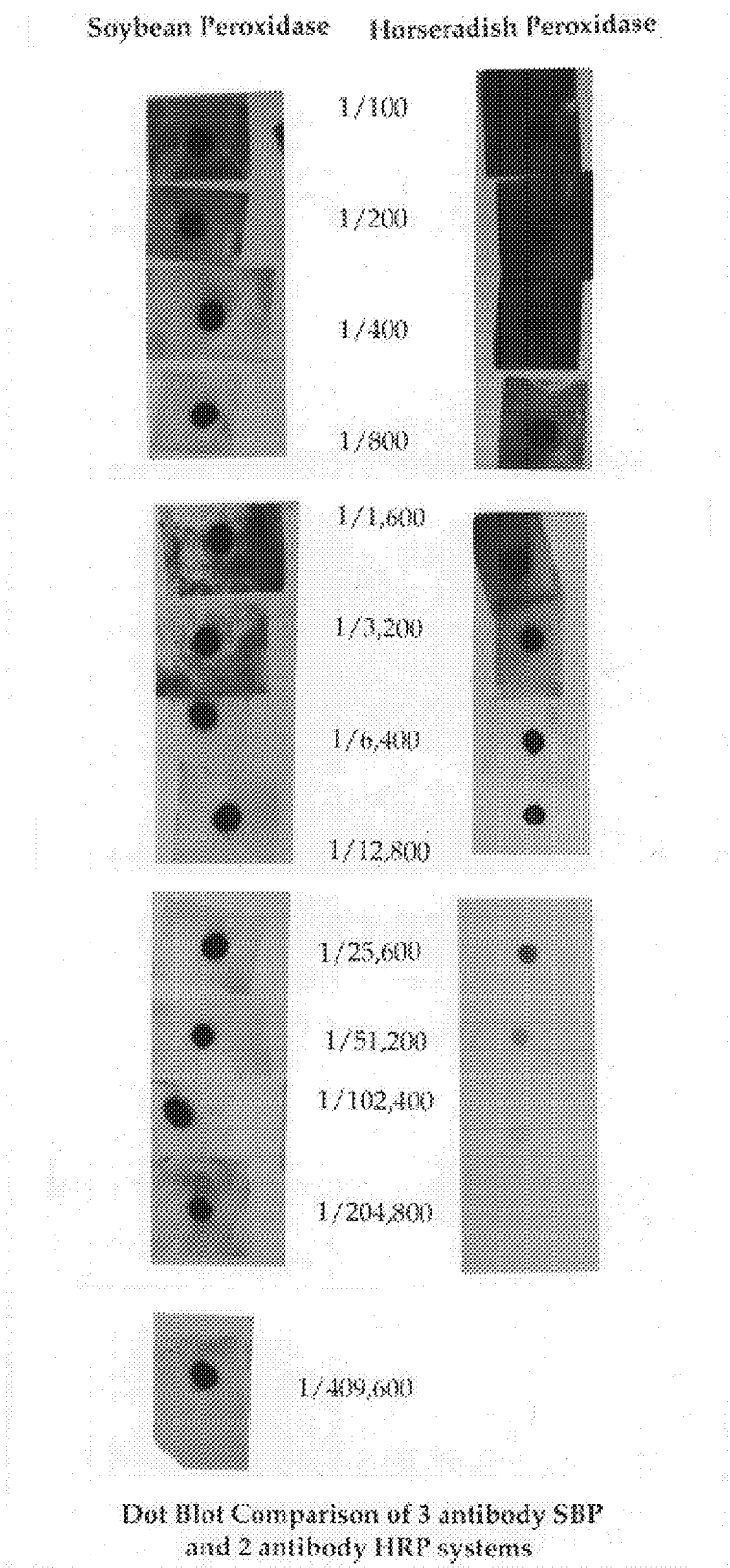
FIG. 12 Immunoblotting procedures using fetuin and MM4 antibody with dot blots used in optimizing antibody concentrations (SPAP on left; HRP on right).

Dot blots were used to determine the best dilution factors and development time. The dot blot data showed the SPAP system have a strong signal with a dilution of 1:409,600 and the HRP system was barely able to detect antigen at a 1:25,600 dilution (FIG. 12). After performing dot blots to optimize the time and dilution factors, an immunoblotting assay was carried out using optimal conditions and the results are shown in FIG. 13. Thus, these results show that the SPAP was at least equal or superior to the HRP reagent. These results suggest that the three antibody system would especially lend itself for kits to be used in field work, and in situations where refreezing is not a practical alterative.

Example 23

Immunoassay Using Non-Conjugated Soybean Peroxidase

A novel technique that uses enzyme anti-enzyme antibody binding instead of antibody enzyme conjugation is described. Crude soybean extracts, containing the lipoxygenase L2 isozyme, were added to microplate wells and incubated overnight at 4° C. and then blocked with a 1% BSA solution. The L2 mouse MAB was used to bind to the mouse L2 enzyme in the sample. A goat antimouse immunoglobulin was used to bind to the mouse L2 antibody. To complete the sandwich, the unconjugated mouse anti-soybean iperoxidase MAB was bound to the goat antimouse. Peroxidase solution was added to the well and peroxidase captured by the anti-soybean peroxidase MAB. A chromogenic substrate was added and the oxidized product read at the appropriate wavelength.

Example 24

Identification of Genomic DNA for Soybean Peroxidases

A soybean genomic DNA library was prepared by digesting DNA isolated from soybean with BamHI and XhoI which was chosen on the basis that it did not cut within the cDNA sequence of the peroxidase genes. The digested genomic DNA was inserted into λZapII which had been digested with BamHI and XhoI which was then used to identify the genomic DNA coding for the soybean peroxidases disclosed above. The cDNA specific primers described above were used to search the genomic library. Positive clones were sequenced and the sequences compared with the cDNA sequences set forth in the Sequence Listing to identify genomic DNA which contained the entire coding region of the cDNA. The genomic sequence for SEPa1 is set forth in FIG. 14 and SEQ ID NO: 18. The ATG start codon at 1392 is underlined. The genomic sequence for SEPb1 is set forth in FIG. 15 and SEQ ID NO:19. The ATG start codon at 981 is underlined. The genomic DNA for each of these soybean peroxidases includes the promoter region. Thus, the promoter for SEPa1 is contained within nucleotides 1 and 1391 of FIG. 14. The promoter for SEPb1 is contained within nucleotides 1 and 980 of FIG. 15.

While the invention has been disclosed in this patent application by reference to the details of the preferred embodiments of the invention, it is to be understood that this disclosure is intended in an illustrative rather than a limiting sense, as it is contemplated that modifications will readily occur to those skilled in the art, within the spirit of the invention and the scope of the appended claims.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

His Phe His Asp Cys Phe Val
1               5

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CAYTTYCAYG AYTGYTT YGT  20

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

AAATTAACTC AGCTGTGGG  19

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGAACCCACT TATTCCATCG  20

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CCCAAGACAT GCTTGAGAT  19

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

AAGTTCATAC TTCTAAC (2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Gln Leu Xaa Xaa Xaa Phe Tyr
1                5

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Ala Ala Thr Ala Ala Ala
1              5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

His Phe His Asp Cys Phe Val
1                5

(2) INFORMATION FOR SEQ ID NO:10:

(i) SEQUENCE CHARACTERISTICS:
        (A) LENGTH: 1314 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..82

(ix) FEATURE:
        (A) NAME/KEY: CDS
        (B) LOCATION: 83..1054

(ix) FEATURE:
        (A) NAME/KEY: 3'UTR
        (B) LOCATION: 1055..1314

(ix) FEATURE:
        (A) NAME/KEY: sig_peptide
        (B) LOCATION: 83..145

(ix) FEATURE:
        (A) NAME/KEY: mat_peptide
        (B) LOCATION: 146..1054

( x i ) SEQUENCE DESCRIPTION: SEQ ID NO:10:

```
GAAGCATCTG AGTGTTTACT ATTTTGTACT ATATTTATAT ATAGTCACTC AAGCTTCTAG                    60

GATTTCTGCC TGCTGCATCA AA ATG GGA AGC AAC TTG AGG TTT TTG AGT CTT                    112
                         Met Gly Ser Asn Leu Arg Phe Leu Ser Leu
                         -21 -20                          -15

TGC CTC TTG GCA TTG ATT GCA TCG ACT CAT GCT CAA CTT CAG CTT GGT                     160
Cys Leu Leu Ala Leu Ile Ala Ser Thr His Ala Gln Leu Gln Leu Gly
    -10                 -5                   1                 5

TTT TAT GCT AAC AGT TGC CCA AAA GCA GAG CAA ATT GTT TTG AAA TTT                     208
Phe Tyr Ala Asn Ser Cys Pro Lys Ala Glu Gln Ile Val Leu Lys Phe
                10              15                       20

GTT CAT GAC CAT ATC CAC AAT GCT CCA TCA CTA GCA GCT GCA TTA ATA                     256
Val His Asp His Ile His Asn Ala Pro Ser Leu Ala Ala Ala Leu Ile
            25              30                       35

AGA ATG CAC TTT CAT GAC TGT TTT GTA AGG GGA TGT GAT GCA TCA GTC                     304
Arg Met His Phe His Asp Cys Phe Val Arg Gly Cys Asp Ala Ser Val
        40              45              50

CTT CTG AAC TCA ACA ACC AAT CAG GCT GAG AAG AAT GCT CCT CCA AAT                     352
Leu Leu Asn Ser Thr Thr Asn Gln Ala Glu Lys Asn Ala Pro Pro Asn
    55              60                  65

CTC ACA GTA AGA GGC TTT GAC TTC ATT GAC AGA ATA AAG AGC CTT GTT                     400
Leu Thr Val Arg Gly Phe Asp Phe Ile Asp Arg Ile Lys Ser Leu Val
70              75              80                       85

GAA GCT GAA TGC CCT GGT GTG GTC TCT TGT GCT GAT ATC CTC ACT TTG                     448
Glu Ala Glu Cys Pro Gly Val Val Ser Cys Ala Asp Ile Leu Thr Leu
                90              95                      100

GCT GCC AGA GAC ACT ATT GTA GCC ACA GGT GGA CCT TTT TGG AAA GTT                     496
Ala Ala Arg Asp Thr Ile Val Ala Thr Gly Gly Pro Phe Trp Lys Val
            105             110                     115

CCA ACT GGT CGA AGG GAT GGG GTC GTC TCT AAC TTG ACG GAA GCC AGA                     544
Pro Thr Gly Arg Arg Asp Gly Val Val Ser Asn Leu Thr Glu Ala Arg
        120             125                 130

AAT AAC ATT CCT GCT CCA TCT TCC AAC TTT ACC ACC CTA CAA ACA CTC                     592
Asn Asn Ile Pro Ala Pro Ser Ser Asn Phe Thr Thr Leu Gln Thr Leu
    135             140                 145

TTT GCT AAC CAA GGA CTT GAT TTG AAG GAC TTG GTC CTG CTC TCT GGT                     640
Phe Ala Asn Gln Gly Leu Asp Leu Lys Asp Leu Val Leu Leu Ser Gly
150             155                 160                     165

GCT CAC ACA ATT GGT ATC GCT CAT TGC TCA TCA TTA TCA AAC CGG TTG                     688
Ala His Thr Ile Gly Ile Ala His Cys Ser Ser Leu Ser Asn Arg Leu
                170             175                     180

TTC AAT TTC ACT GGC AAG GGT GAT CAA GAC CCG TCA CTA GAT AGT GAA                     736
Phe Asn Phe Thr Gly Lys Gly Asp Gln Asp Pro Ser Leu Asp Ser Glu
            185             190                     195

TAT GCT GCA AAT TTG AAA GCA TTC AAG TGC ACA GAC CTC AAC AAG TTG                     784
Tyr Ala Ala Asn Leu Lys Ala Phe Lys Cys Thr Asp Leu Asn Lys Leu
        200             205                 210

AAC ACC ACA AAA ATT GAG ATG GAC CCT GGA AGT CGC AAG ACA TTT GAT                     832
Asn Thr Thr Lys Ile Glu Met Asp Pro Gly Ser Arg Lys Thr Phe Asp
    215             220                 225

CTT AGC TAC TAT AGT CAC GTT ATT AAG AGA AGG GGT CTA TTT GAG TCA                     880
Leu Ser Tyr Tyr Ser His Val Ile Lys Arg Arg Gly Leu Phe Glu Ser
230             235                 240                     245

GAT GCT GCA TTA TTG ACT AAC TCA GTT ACA AAG GCA CAA ATC ATC CAA                     928
Asp Ala Ala Leu Leu Thr Asn Ser Val Thr Lys Ala Gln Ile Ile Gln
                250             255                     260

TTG CTT GAA GGG TCA GTT GAA AAT TTC TTT GCT GAG TTT GCA ACC TCC                     976
Leu Leu Glu Gly Ser Val Glu Asn Phe Phe Ala Glu Phe Ala Thr Ser
            265             270                     275
```

```
ATC GAG AAA ATG GGA AGA ATT AAT GTG AAG ACA GGC ACA GAA GGA GAG         1024
Ile Glu Lys Met Gly Arg Ile Asn Val Lys Thr Gly Thr Glu Gly Glu
        280                     285                 290

ATC AGG AAG CAT TGT GCA TTT ATA AAT AGC TAAGAATCTT GTCTTGGGGT           1074
Ile Arg Lys His Cys Ala Phe Ile Asn Ser
        295                 300

TTGATTATTT ATGCTATGCC ATGTTTTTG ATTAGTTATG CTATGCCATG TGGTCTCTGT        1134

CTACATACGT GTGATCCTTT ATGGTATGGT TGTTGTATGT GTGTTGGAAT AAGTGGGCTC       1194

TTAAGTTATT CATATTTCCA ACTTTCCAAC TTTGCTGGTA GATCATGCTC TTGTAATAAG       1254

AACCAGAATT TTTTGTGCTA CCCACAGCTG AGTTAATTTA AAAAAAAAAA AAAAAAAAA        1314
```

( 2 ) INFORMATION FOR SEQ ID NO:11:

( i ) SEQUENCE CHARACTERISTICS:
        ( A ) LENGTH: 324 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Gly Ser Asn Leu Arg Phe Leu Ser Leu Cys Leu Leu Ala Leu Ile
-21     -20             -15             -10

Ala Ser Thr His Ala Gln Leu Gln Leu Gly Phe Tyr Ala Asn Ser Cys
 -5              1               5                       10

Pro Lys Ala Glu Gln Ile Val Leu Lys Phe Val His Asp His Ile His
            15              20                  25

Asn Ala Pro Ser Leu Ala Ala Ala Leu Ile Arg Met His Phe His Asp
        30              35              40

Cys Phe Val Arg Gly Cys Asp Ala Ser Val Leu Leu Asn Ser Thr Thr
    45              50              55

Asn Gln Ala Glu Lys Asn Ala Pro Pro Asn Leu Thr Val Arg Gly Phe
60              65              70                      75

Asp Phe Ile Asp Arg Ile Lys Ser Leu Val Glu Ala Glu Cys Pro Gly
            80              85                      90

Val Val Ser Cys Ala Asp Ile Leu Thr Leu Ala Ala Arg Asp Thr Ile
        95              100             105

Val Ala Thr Gly Gly Pro Phe Trp Lys Val Pro Thr Gly Arg Arg Asp
        110             115             120

Gly Val Val Ser Asn Leu Thr Glu Ala Arg Asn Asn Ile Pro Ala Pro
    125             130             135

Ser Ser Asn Phe Thr Thr Leu Gln Thr Leu Phe Ala Asn Gln Gly Leu
140             145             150                     155

Asp Leu Lys Asp Leu Val Leu Leu Ser Gly Ala His Thr Ile Gly Ile
            160             165             170

Ala His Cys Ser Ser Leu Ser Asn Arg Leu Phe Asn Phe Thr Gly Lys
        175             180             185

Gly Asp Gln Asp Pro Ser Leu Asp Ser Glu Tyr Ala Ala Asn Leu Lys
        190             195             200

Ala Phe Lys Cys Thr Asp Leu Asn Lys Leu Asn Thr Thr Lys Ile Glu
    205             210             215

Met Asp Pro Gly Ser Arg Lys Thr Phe Asp Leu Ser Tyr Tyr Ser His
220             225             230                     235

Val Ile Lys Arg Arg Gly Leu Phe Glu Ser Asp Ala Ala Leu Leu Thr
            240             245             250
```

| | | | | | | | | | | | | | | | |
|---|---|---|---|---|---|---|---|---|---|---|---|---|---|---|---|
|Asn|Ser|Val|Thr|Lys|Ala|Gln|Ile|Ile|Gln|Leu|Leu|Glu|Gly|Ser|Val|
| | | |255| | | |260| | | | |265| | | |
|Glu|Asn|Phe|Phe|Ala|Glu|Phe|Ala|Thr|Ser|Ile|Glu|Lys|Met|Gly|Arg|
| | |270| | | |275| | | | |280| | | | |
|Ile|Asn|Val|Lys|Thr|Gly|Thr|Glu|Gly|Glu|Ile|Arg|Lys|His|Cys|Ala|
| |285| | | | |290| | | | |295| | | | |
|Phe|Ile|Asn|Ser| | | | | | | | | | | | |
|300| | | | | | | | | | | | | | | |

(2) INFORMATION FOR SEQ ID NO:12:

(i) SEQUENCE CHARACTERISTICS:
        (A) LENGTH: 1326 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..86

(ix) FEATURE:
        (A) NAME/KEY: CDS
        (B) LOCATION: 87..1058

(ix) FEATURE:
        (A) NAME/KEY: 3'UTR
        (B) LOCATION: 1059..1326

(ix) FEATURE:
        (A) NAME/KEY: sig_peptide
        (B) LOCATION: 87..149

(ix) FEATURE:
        (A) NAME/KEY: mat_peptide
        (B) LOCATION: 150..1058

(xi) SEQUENCE DESCRIPTION: SEQ ID NO:12:

```
GCCTCTTTCA AGAAGCATCT GAGTGCTTAT TATTTGTAAT ATATATAGTC ACTCAAGCTT          60

CTAGGATTTG TGCCAGCTAC ATGAAA ATG GGA AGC AAC TTC AGG TTT TTG AGT         113
                             Met Gly Ser Asn Phe Arg Phe Leu Ser
                             -21 -20                     -15

CTT TGC CTC TTG GCA TTG ATT GCA TCA ACC CAT GCT CAA CTT CAG CTT          161
Leu Cys Leu Leu Ala Leu Ile Ala Ser Thr His Ala Gln Leu Gln Leu
        -10                  -5                   1

GGT TTT TAT GCC AAG AGT TGC CCA AAC GCT GAG CAA ATC GTT TTG AAA          209
Gly Phe Tyr Ala Lys Ser Cys Pro Asn Ala Glu Gln Ile Val Leu Lys
 5                   10                  15                  20

TTT GTC CAT GAC CAT ATC CAC AAT GCT CCA TCA CTA GCA GCT GCA TTG          257
Phe Val His Asp His Ile His Asn Ala Pro Ser Leu Ala Ala Ala Leu
                25                  30                  35

ATA AGA ATG CAC TTC CAT GAC TGT TTT GTA AGG GGA TGT GAT GCA TCA          305
Ile Arg Met His Phe His Asp Cys Phe Val Arg Gly Cys Asp Ala Ser
            40                  45                  50

GTC CTT CTG AAC TCA ACA ACC AAT CAA GCT GAA AAG AAT GCT CCT CCA          353
Val Leu Leu Asn Ser Thr Thr Asn Gln Ala Glu Lys Asn Ala Pro Pro
        55                  60                  65

AAT CTC ACA GTA AGA GGC TTT GAC TTC ATT GAC AGA ATA AAG AGC CTT          401
Asn Leu Thr Val Arg Gly Phe Asp Phe Ile Asp Arg Ile Lys Ser Leu
    70                  75                  80

GTT GAG GCA GAA TGC CCT GGT GTG GTC TCT TGT GCT GAT ATC CTC ACT          449
Val Glu Ala Glu Cys Pro Gly Val Val Ser Cys Ala Asp Ile Leu Thr
85                  90                  95                  100

TTG TCT GCC AGA GAC ACT ATT GTA GCC ACA GGT GGA CCA TTT TGG AAA          497
```

|  |  |  |  |  |  |  |  |  |  |  |  |  |  |  |  |
|---|---|---|---|---|---|---|---|---|---|---|---|---|---|---|---|
| Leu | Ser | Ala | Arg | Asp<br>105 | Thr | Ile | Val | Ala | Thr<br>110 | Gly | Gly | Pro | Phe | Trp<br>115 | Lys |

| GTT | CCA | ACA | GGT | CGA | AGA | GAT | GGG | GTC | ATC | TCT | AAC | TTG | ACG | GAA | GCC | 545 |
|---|---|---|---|---|---|---|---|---|---|---|---|---|---|---|---|---|
| Val | Pro | Thr | Gly<br>120 | Arg | Arg | Asp | Gly | Val<br>125 | Ile | Ser | Asn | Leu | Thr<br>130 | Glu | Ala | |

| AGA | GAT | AAC | ATT | CCT | GCT | CCA | TCT | TCT | AAC | TTT | ACC | ACC | CTA | CAA | ACA | 593 |
| Arg | Asp | Asn<br>135 | Ile | Pro | Ala | Pro | Ser | Ser<br>140 | Asn | Phe | Thr | Thr<br>145 | Leu | Gln | Thr | |

| CTC | TTT | GCC | AAC | CAA | GGA | CTT | GAT | TTG | AAG | GAC | TTG | GTC | CTG | CTC | TCT | 641 |
| Leu | Phe<br>150 | Ala | Asn | Gln | Gly | Leu<br>155 | Asp | Leu | Lys | Asp | Leu<br>160 | Val | Leu | Leu | Ser | |

| GGT | GCT | CAC | ACA | ATT | GGT | ATC | GCT | CAT | TGC | TCA | TCA | TTG | TCA | AAC | CGC | 689 |
| Gly | Ala | His | Thr | Ile<br>170 | Gly | Ile | Ala | His | Cys | Ser<br>175 | Ser | Leu | Ser | Asn | Arg<br>180 | |
| 165 | | | | | | | | | | | | | | | | |

| TTG | TTC | AAT | TTC | ACT | GGC | AAG | GGT | GAT | CAA | GAC | CCG | TCA | TTA | GAC | AGT | 737 |
| Leu | Phe | Asn | Phe | Thr<br>185 | Gly | Lys | Gly | Asp | Gln<br>190 | Asp | Pro | Ser | Leu | Asp<br>195 | Ser | |

| GAA | TAT | GCT | GCA | AAT | CTG | AAA | GCC | TTC | AAG | TGC | ACG | GAC | CTC | AAT | AAG | 785 |
| Glu | Tyr | Ala | Ala<br>200 | Asn | Leu | Lys | Ala | Phe<br>205 | Lys | Cys | Thr | Asp | Leu<br>210 | Asn | Lys | |

| TTG | AAC | ACC | ACA | AAA | ATT | GAG | ATG | GAC | CCT | GGA | AGT | CGC | AAG | ACA | TTT | 833 |
| Leu | Asn | Thr<br>215 | Thr | Lys | Ile | Glu | Met<br>220 | Asp | Pro | Gly | Ser | Arg<br>225 | Lys | Thr | Phe | |

| GAT | CTT | AGC | TAC | TAT | AGT | CAT | GTG | ATT | AAG | AGA | AGG | GGT | CTA | TTT | GAG | 881 |
| Asp | Leu<br>230 | Ser | Tyr | Tyr | Ser | His<br>235 | Val | Ile | Lys | Arg | Arg<br>240 | Gly | Leu | Phe | Glu | |

| TCA | GAT | GCT | GCA | TTG | TTG | ACA | AAC | TCA | GTT | ACA | AAG | GCT | CAA | ATC | ATT | 929 |
| Ser<br>245 | Asp | Ala | Ala | Leu | Leu<br>250 | Thr | Asn | Ser | Val | Thr<br>255 | Lys | Ala | Gln | Ile | Ile<br>260 | |

| GAA | TTG | CTT | GAA | GGG | TCA | GTT | GAA | AAT | TTC | TTT | GCT | GAG | TTT | GCA | ACC | 977 |
| Glu | Leu | Leu | Glu | Gly<br>265 | Ser | Val | Glu | Asn | Phe<br>270 | Phe | Ala | Glu | Phe | Ala<br>275 | Thr | |

| TCC | ATG | GAG | AAA | ATG | GGA | AGA | ATT | AAT | GTA | AAG | ACA | GGG | ACA | GAA | GGA | 1025 |
| Ser | Met | Glu | Lys<br>280 | Met | Gly | Arg | Ile | Asn<br>285 | Val | Lys | Thr | Gly | Thr<br>290 | Glu | Gly | |

| GAG | ATC | AGG | AAG | CAT | TGT | GCA | TTT | CTA | AAT | AGC | TAAGAATCTT | GTCTTGTTCA | 1078 |
| Glu | Ile | Arg<br>295 | Lys | His | Cys | Ala | Phe<br>300 | Leu | Asn | Ser | | | |

| TGGATGAATC | TTGTATCATT | TATTTTTGG | GTTTGGTTAT | TTATGCTATG | CCATGTTTTT | 1138 |
|---|---|---|---|---|---|---|
| TTATTAGTTA | TGCTATGCCA | TGTGGTGTCT | GTCTACATAT | GAGTGATCCC | GTATGGTATG | 1198 |
| GTTGTTGTAT | GTGCGATGGA | ATAAGTGGGT | TCCATTGTTA | TTCTTATAAT | TTCCAACTTT | 1258 |
| GCTGGTAGAT | CTTGTAATAA | GAAGCAGAAT | TTCTTGTGCT | AAAAAAAAAA | AAAAAAAAA | 1318 |
| AAAAAAAA | | | | | | 1326 |

( 2 ) INFORMATION FOR SEQ ID NO:13:

( i ) SEQUENCE CHARACTERISTICS:
        ( A ) LENGTH: 324 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| Met<br>-21 | Gly | Ser<br>-20 | Asn | Phe | Arg | Phe<br>-15 | Leu | Ser | Leu | Cys | Leu<br>-10 | Leu | Ala | Leu | Ile |
|---|---|---|---|---|---|---|---|---|---|---|---|---|---|---|---|
| Ala | Ser<br>-5 | Thr | His | Ala | Gln<br>1 | Leu | Gln | Leu | Gly<br>5 | Phe | Tyr | Ala | Lys | Ser<br>10 | Cys |
| Pro | Asn | Ala | Glu | Gln | Ile | Val | Leu | Lys | Phe | Val | His | Asp | His | Ile | His |

|  | 15 | 20 | 25 |
|---|---|---|---|

Asn Ala Pro Ser Leu Ala Ala Ala Leu Ile Arg Met His Phe His Asp
　　　　30　　　　　　　　　35　　　　　　　　　40

Cys Phe Val Arg Gly Cys Asp Ala Ser Val Leu Leu Asn Ser Thr Thr
　　　45　　　　　　　　50　　　　　　　　　　55

Asn Gln Ala Glu Lys Asn Ala Pro Pro Asn Leu Thr Val Arg Gly Phe
60　　　　　　　　　65　　　　　　　　　　70　　　　　　　　　　75

Asp Phe Ile Asp Arg Ile Lys Ser Leu Val Glu Ala Glu Cys Pro Gly
　　　　　　　　80　　　　　　　　　　85　　　　　　　　　　　90

Val Val Ser Cys Ala Asp Ile Leu Thr Leu Ser Ala Arg Asp Thr Ile
　　　　　　95　　　　　　　　　　100　　　　　　　　　105

Val Ala Thr Gly Gly Pro Phe Trp Lys Val Pro Thr Gly Arg Arg Asp
　　　　110　　　　　　　　　115　　　　　　　　　120

Gly Val Ile Ser Asn Leu Thr Glu Ala Arg Asp Asn Ile Pro Ala Pro
　　　125　　　　　　　　　130　　　　　　　　　135

Ser Ser Asn Phe Thr Thr Leu Gln Thr Leu Phe Ala Asn Gln Gly Leu
140　　　　　　　　　145　　　　　　　　　　150　　　　　　　　　155

Asp Leu Lys Asp Leu Val Leu Leu Ser Gly Ala His Thr Ile Gly Ile
　　　　　　　　　160　　　　　　　　　165　　　　　　　　　170

Ala His Cys Ser Ser Leu Ser Asn Arg Leu Phe Asn Phe Thr Gly Lys
　　　　　　175　　　　　　　　　　180　　　　　　　　　185

Gly Asp Gln Asp Pro Ser Leu Asp Ser Glu Tyr Ala Ala Asn Leu Lys
　　　　　190　　　　　　　　　195　　　　　　　　　200

Ala Phe Lys Cys Thr Asp Leu Asn Lys Leu Asn Thr Thr Lys Ile Glu
　　　205　　　　　　　　　　210　　　　　　　　　　215

Met Asp Pro Gly Ser Arg Lys Thr Phe Asp Leu Ser Tyr Tyr Ser His
220　　　　　　　　　　225　　　　　　　　　　230　　　　　　　　　235

Val Ile Lys Arg Arg Gly Leu Phe Glu Ser Asp Ala Ala Leu Leu Thr
　　　　　　　240　　　　　　　　　　245　　　　　　　　　250

Asn Ser Val Thr Lys Ala Gln Ile Ile Glu Leu Leu Glu Gly Ser Val
　　　　　　255　　　　　　　　　260　　　　　　　　　265

Glu Asn Phe Phe Ala Glu Phe Ala Thr Ser Met Glu Lys Met Gly Arg
　　　　270　　　　　　　　　275　　　　　　　　　280

Ile Asn Val Lys Thr Gly Thr Glu Gly Glu Ile Arg Lys His Cys Ala
　　285　　　　　　　　　290　　　　　　　　　295

Phe Leu Asn Ser
300

( 2 ) INFORMATION FOR SEQ ID NO:14:

( i ) SEQUENCE CHARACTERISTICS:
  ( A ) LENGTH: 1191 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 60..998

( i x ) FEATURE:
  ( A ) NAME/KEY: 5'UTR
  ( B ) LOCATION: 1..59

( i x ) FEATURE:
  ( A ) NAME/KEY: 3'UTR
  ( B ) LOCATION: 999..1191

( i x ) FEATURE:

-continued (A) NAME/KEY: sig_peptide
(B) LOCATION: 60..122

(ix) FEATURE:
(A) NAME/KEY: mat_peptide
(B) LOCATION: 123..998

(xi) SEQUENCE DESCRIPTION: SEQ ID NO:14:

```
GGCACGAGGA GAGAGAGAGA GAGAGAACTA GTCTCGAGCA TCAAAGTACT CAAATTAGC                          59

ATG  GCT  GTC  ATG  GTT  GCA  TTC  TTG  AAT  TTG  ATC  ATC  TTT  TCA  GTA  GTC           107
Met  Ala  Val  Met  Val  Ala  Phe  Leu  Asn  Leu  Ile  Ile  Phe  Ser  Val  Val
-21  -20                      -15                      -10

TCT  ACA  ACA  GGC  AAG  TCA  CTG  AGC  TTA  AAC  TAC  TAT  GCA  AAA  ACA  TGC           155
Ser  Thr  Thr  Gly  Lys  Ser  Leu  Ser  Leu  Asn  Tyr  Tyr  Ala  Lys  Thr  Cys
-5                    1                    5                         10

CCT  AAT  GTG  GAG  TTC  ATT  GTT  GCC  AAG  GCA  GTA  AAG  GAT  GCC  ACT  GCT           203
Pro  Asn  Val  Glu  Phe  Ile  Val  Ala  Lys  Ala  Val  Lys  Asp  Ala  Thr  Ala
                    15                   20                        25

AGG  GAC  AAA  ACT  GTT  CCA  GCA  GCA  ATT  CTG  CGA  ATG  CAC  TTC  CAT  GAT           251
Arg  Asp  Lys  Thr  Val  Pro  Ala  Ala  Ile  Leu  Arg  Met  His  Phe  His  Asp
               30                        35                   40

TGT  TTC  GTT  CGG  GGG  TGT  GAT  GCC  TCT  GTG  CTG  CTA  AAT  TCA  AAA  GGA           299
Cys  Phe  Val  Arg  Gly  Cys  Asp  Ala  Ser  Val  Leu  Leu  Asn  Ser  Lys  Gly
          45                        50                   55

AAC  AAC  AAA  GCA  GAA  AAA  GAC  GGG  CCA  CCA  AAT  GTT  TCT  TTG  CAT  GCA           347
Asn  Asn  Lys  Ala  Glu  Lys  Asp  Gly  Pro  Pro  Asn  Val  Ser  Leu  His  Ala
60                        65                        70                        75

TTC  TAT  GTC  ATT  GTA  GCA  GCA  AAG  AAA  GCA  CTA  GAA  GCT  TCA  TGC  CCT           395
Phe  Tyr  Val  Ile  Val  Ala  Ala  Lys  Lys  Ala  Leu  Glu  Ala  Ser  Cys  Pro
                    80                        85                        90

GGT  GTG  GTC  TCT  TGT  GCT  GAC  ATC  CTT  GCT  CTG  GCA  GCA  AGG  GTC  GCA           443
Gly  Val  Val  Ser  Cys  Ala  Asp  Ile  Leu  Ala  Leu  Ala  Ala  Arg  Val  Ala
               95                       100                       105

GTT  TTT  CTG  TCA  GGA  GGA  CCT  ACA  TGG  GAT  GTT  CCT  AAA  GGA  AGA  AAG           491
Val  Phe  Leu  Ser  Gly  Gly  Pro  Thr  Trp  Asp  Val  Pro  Lys  Gly  Arg  Lys
          110                       115                       120

GAT  GGT  AGA  ACA  TCT  AAA  GCC  AGT  GAA  ACC  AGA  CAA  TTG  CCA  GCA  CCA           539
Asp  Gly  Arg  Thr  Ser  Lys  Ala  Ser  Glu  Thr  Arg  Gln  Leu  Pro  Ala  Pro
     125                       130                       135

ACC  TTC  AAC  TTA  TCA  CAA  CTG  CGG  CAA  AGT  TTC  TCT  CAA  AGA  GGA  CTG           587
Thr  Phe  Asn  Leu  Ser  Gln  Leu  Arg  Gln  Ser  Phe  Ser  Gln  Arg  Gly  Leu
140                       145                       150                       155

TCA  GGG  GAA  GAC  CTG  GTA  GCT  CTG  TCA  GGG  GGG  CAC  ACT  TTG  GGT  TTC           635
Ser  Gly  Glu  Asp  Leu  Val  Ala  Leu  Ser  Gly  Gly  His  Thr  Leu  Gly  Phe
                    160                       165                       170

TCT  CAC  TGC  TCA  TCT  TTC  AAG  AAC  AGA  ATC  CAC  AAC  TTC  AAT  GCA  ACA           683
Ser  His  Cys  Ser  Ser  Phe  Lys  Asn  Arg  Ile  His  Asn  Phe  Asn  Ala  Thr
               175                       180                       185

CAT  GAT  GTT  GAC  CCT  TCA  TTA  AAT  CCA  TCA  TTT  GCA  GCA  AAA  CTG  ATC           731
His  Asp  Val  Asp  Pro  Ser  Leu  Asn  Pro  Ser  Phe  Ala  Ala  Lys  Leu  Ile
          190                       195                       200

TCA  ATT  TGT  CCA  CTA  AAA  AAT  CAG  GCA  AAA  AAT  GCA  GGC  ACC  TCT  ATG           779
Ser  Ile  Cys  Pro  Leu  Lys  Asn  Gln  Ala  Lys  Asn  Ala  Gly  Thr  Ser  Met
     205                       210                       215

GAC  CCT  TCA  ACA  ACA  ACT  TTT  GAT  AAT  ACA  TAT  TAC  AGG  TTG  ATC  CTC           827
Asp  Pro  Ser  Thr  Thr  Thr  Phe  Asp  Asn  Thr  Tyr  Tyr  Arg  Leu  Ile  Leu
220                       225                       230                       235

CAA  CAG  AAA  GGC  TTG  TTT  TCT  TCT  GAT  CAA  GTT  TTG  CTT  GAC  AAC  CCA           875
Gln  Gln  Lys  Gly  Leu  Phe  Ser  Ser  Asp  Gln  Val  Leu  Leu  Asp  Asn  Pro
                    240                       245                       250

GAC  ACT  AAA  AAT  CTG  GTT  ACA  AAG  TTT  GCC  ACC  TCA  AAA  AAG  GCT  TTT           923
```

```
Asp  Thr  Lys  Asn  Leu  Val  Thr  Lys  Phe  Ala  Thr  Ser  Lys  Lys  Ala  Phe
          255                 260                 265

TAT  GAG  GCT  TTT  GCG  AAG  TCC  ATG  ATC  AGA  ATG  AGT  AGC  TAC  AAT  GGT         971
Tyr  Glu  Ala  Phe  Ala  Lys  Ser  Met  Ile  Arg  Met  Ser  Ser  Tyr  Asn  Gly
          270                 275                 280

GGA  CAG  GAG  GTT  AGA  AGG  ACT  GCA  GAA  TGATCAATTA  ATAAGTCTTA                   1018
Gly  Gln  Glu  Val  Arg  Arg  Thr  Ala  Glu
          285                 290

AATCAATTCA  AGTTAAATTG  ATGTTCCAAA  CAAGTTGGAT  CAAATTTCCT  AGATGCCAAG                1078

ATATTATGTC  TTTTTCCTCT  ATTAAAGAAA  TATGTATATT  TATCTGAAGT  TAATAAAATC                1138

TCAAGCATGT  CTTGGGAAAT  TAATTTAGAG  CTCAAAAAAA  AAAAAAAAAA  AAA                       1191
```

( 2 ) INFORMATION FOR SEQ ID NO:15:

( i ) SEQUENCE CHARACTERISTICS:
        ( A ) LENGTH: 313 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Ala  Val  Met  Val  Ala  Phe  Leu  Asn  Leu  Ile  Ile  Phe  Ser  Val  Val
-21       -20                 -15                 -10

Ser  Thr  Thr  Gly  Lys  Ser  Leu  Ser  Leu  Asn  Tyr  Tyr  Ala  Lys  Thr  Cys
-5                       1                   5                       10

Pro  Asn  Val  Glu  Phe  Ile  Val  Ala  Lys  Ala  Val  Lys  Asp  Ala  Thr  Ala
               15                  20                  25

Arg  Asp  Lys  Thr  Val  Pro  Ala  Ala  Ile  Leu  Arg  Met  His  Phe  His  Asp
          30                  35                  40

Cys  Phe  Val  Arg  Gly  Cys  Asp  Ala  Ser  Val  Leu  Leu  Asn  Ser  Lys  Gly
     45                  50                  55

Asn  Asn  Lys  Ala  Glu  Lys  Asp  Gly  Pro  Pro  Asn  Val  Ser  Leu  His  Ala
60                  65                  70                            75

Phe  Tyr  Val  Ile  Val  Ala  Ala  Lys  Lys  Ala  Leu  Glu  Ala  Ser  Cys  Pro
               80                  85                  90

Gly  Val  Val  Ser  Cys  Ala  Asp  Ile  Leu  Ala  Leu  Ala  Ala  Arg  Val  Ala
               95                  100                 105

Val  Phe  Leu  Ser  Gly  Gly  Pro  Thr  Trp  Asp  Val  Pro  Lys  Gly  Arg  Lys
          110                 115                 120

Asp  Gly  Arg  Thr  Ser  Lys  Ala  Ser  Glu  Thr  Arg  Gln  Leu  Pro  Ala  Pro
     125                 130                 135

Thr  Phe  Asn  Leu  Ser  Gln  Leu  Arg  Gln  Ser  Phe  Ser  Gln  Arg  Gly  Leu
140                 145                 150                           155

Ser  Gly  Glu  Asp  Leu  Val  Ala  Leu  Ser  Gly  Gly  His  Thr  Leu  Gly  Phe
               160                 165                 170

Ser  His  Cys  Ser  Ser  Phe  Lys  Asn  Arg  Ile  His  Asn  Phe  Asn  Ala  Thr
               175                 180                 185

His  Asp  Val  Asp  Pro  Ser  Leu  Asn  Pro  Ser  Phe  Ala  Ala  Lys  Leu  Ile
          190                 195                 200

Ser  Ile  Cys  Pro  Leu  Lys  Asn  Gln  Ala  Lys  Asn  Ala  Gly  Thr  Ser  Met
     205                 210                 215

Asp  Pro  Ser  Thr  Thr  Thr  Phe  Asp  Asn  Thr  Tyr  Tyr  Arg  Leu  Ile  Leu
220                 225                 230                           235

Gln  Gln  Lys  Gly  Leu  Phe  Ser  Ser  Asp  Gln  Val  Leu  Leu  Asp  Asn  Pro
               240                 245                 250
```

| | | | | | | | | | | | | | | |
|---|---|---|---|---|---|---|---|---|---|---|---|---|---|---|
| Asp | Thr | Lys | Asn | Leu | Val | Thr | Lys | Phe | Ala | Thr | Ser | Lys | Lys | Ala | Phe |
| | | | 255 | | | | | 260 | | | | | 265 | | |
| Tyr | Glu | Ala | Phe | Ala | Lys | Ser | Met | Ile | Arg | Met | Ser | Ser | Tyr | Asn | Gly |
| | | 270 | | | | | 275 | | | | | 280 | | | |
| Gly | Gln | Glu | Val | Arg | Arg | Thr | Ala | Glu | | | | | | | |
| | 285 | | | | | 290 | | | | | | | | | |

( 2 ) INFORMATION FOR SEQ ID NO:16:

( i ) SEQUENCE CHARACTERISTICS:
        ( A ) LENGTH: 1167 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..38

( i x ) FEATURE:
        ( A ) NAME/KEY: CDS
        ( B ) LOCATION: 39..977

( i x ) FEATURE:
        ( A ) NAME/KEY: 3'UTR
        ( B ) LOCATION: 978..1167

( i x ) FEATURE:
        ( A ) NAME/KEY: sig_peptide
        ( B ) LOCATION: 39..101

( i x ) FEATURE:
        ( A ) NAME/KEY: mat_peptide
        ( B ) LOCATION: 102..977

( x i ) SEQUENCE DESCRIPTION: SEQ ID NO:16:

| | | | | | | | | | | | | | | | |
|---|---|---|---|---|---|---|---|---|---|---|---|---|---|---|---|
| GGCACGAGGC | TAAAAATCAT | CGAAGTACTC | AAATTAGC | ATG | GCT | GTC | ATG | GTT | | | | | | | 53 |
| | | | | Met | Ala | Val | Met | Val | | | | | | | |
| | | | | -21 | | | | -20 | | | | | | | |
| GCA | TTC | TTG | AAT | TTG | ATC | ATC | ATG | TTT | TCA | GTA | GTC | TCT | ACA | AGC | AAG | 101 |
| Ala | Phe | Leu | Asn | Leu | Ile | Ile | Met | Phe | Ser | Val | Val | Ser | Thr | Ser | Lys |
| | -15 | | | | | -10 | | | | | -5 | | | | |
| TCA | CTG | AGC | TTA | AAC | TAC | TAT | TCA | AAA | ACA | TGC | CCT | GAT | GTG | GAA | TGC | 149 |
| Ser | Leu | Ser | Leu | Asn | Tyr | Tyr | Ser | Lys | Thr | Cys | Pro | Asp | Val | Glu | Cys |
| 1 | | | | 5 | | | | | 10 | | | | | 15 | |
| ATT | GTT | GCC | AAG | GCA | GTG | AAG | GAT | GCC | ACT | GCT | AGG | GAC | AAA | ACT | GTT | 197 |
| Ile | Val | Ala | Lys | Ala | Val | Lys | Asp | Ala | Thr | Ala | Arg | Asp | Lys | Thr | Val |
| | | | 20 | | | | | 25 | | | | | 30 | | |
| CCA | GCT | GCA | CTT | CTG | CGA | ATG | CAC | TTC | CAT | GAC | TGT | TTC | GTT | CGG | GGG | 245 |
| Pro | Ala | Ala | Leu | Leu | Arg | Met | His | Phe | His | Asp | Cys | Phe | Val | Arg | Gly |
| | | 35 | | | | | 40 | | | | | 45 | | | |
| TGT | GGT | GCC | TCT | GTG | CTG | CTA | AAT | TCA | AAA | GGA | AGC | AAC | AAA | GCA | GAA | 293 |
| Cys | Gly | Ala | Ser | Val | Leu | Leu | Asn | Ser | Lys | Gly | Ser | Asn | Lys | Ala | Glu |
| | | 50 | | | | | 55 | | | | | 60 | | | |
| AAA | GAT | GGG | CCA | CCA | AAT | GTT | TCT | TTG | CAT | GCA | TTC | TAT | GTC | ATT | GAT | 341 |
| Lys | Asp | Gly | Pro | Pro | Asn | Val | Ser | Leu | His | Ala | Phe | Tyr | Val | Ile | Asp |
| 65 | | | | | 70 | | | | | 75 | | | | | 80 |
| GCA | GCG | AAG | AAA | GCA | CTA | GAA | GCT | TCA | TGC | CCA | GGT | GTG | GTC | TCT | TGT | 389 |
| Ala | Ala | Lys | Lys | Ala | Leu | Glu | Ala | Ser | Cys | Pro | Gly | Val | Val | Ser | Cys |
| | | | | 85 | | | | | 90 | | | | | 95 | |
| GCT | GAC | ATC | CTT | GCT | CTA | GCA | GCA | AGG | GAT | GCA | GTT | TTT | CTG | TCA | GGA | 437 |
| Ala | Asp | Ile | Leu | Ala | Leu | Ala | Ala | Arg | Asp | Ala | Val | Phe | Leu | Ser | Gly |
| | | | 100 | | | | | 105 | | | | | 110 | | |
| GGA | CCT | ACA | TGG | GAT | GAA | CCT | AAA | GGA | AGA | AAG | GAT | GGC | AGA | ACA | TCT | 485 |
| Gly | Pro | Thr | Trp | Asp | Glu | Pro | Lys | Gly | Arg | Lys | Asp | Gly | Arg | Thr | Ser |

```
                    115                          120                          125
AAA  GCC  AGC  GAA  ACC  AGA  CAA  TTA  CCA  GCA  CCA  ACC  TTC  AAC  TTA  TCA            533
Lys  Ala  Ser  Glu  Thr  Arg  Gln  Leu  Pro  Ala  Pro  Thr  Phe  Asn  Leu  Ser
     130                      135                      140

CAA  CTG  CGG  CAA  AGC  TTT  TCT  CAA  AGA  GGA  CTG  TCA  GGG  GAA  GAC  CTG            581
Gln  Leu  Arg  Gln  Ser  Phe  Ser  Gln  Arg  Gly  Leu  Ser  Gly  Glu  Asp  Leu
145                 150                      155                           160

GTA  GCT  CTG  TCA  GGG  GGG  CAC  ACT  TTG  GGT  TTC  TCT  CAC  TGC  TCA  TCT            629
Val  Ala  Leu  Ser  Gly  Gly  His  Thr  Leu  Gly  Phe  Ser  His  Cys  Ser  Ser
               165                           170                     175

TTC  AAG  AAC  AGA  ATC  CAC  AAC  TTC  AAT  GCT  ACA  CAT  GAT  GAA  GAC  CCT            677
Phe  Lys  Asn  Arg  Ile  His  Asn  Phe  Asn  Ala  Thr  His  Asp  Glu  Asp  Pro
                    180                      185                 190

TCA  TTA  AAT  CCA  TCA  TTT  GCA  ACA  AAA  CTG  ATA  TCA  ATT  TGT  CCA  CTA            725
Ser  Leu  Asn  Pro  Ser  Phe  Ala  Thr  Lys  Leu  Ile  Ser  Ile  Cys  Pro  Leu
               195                      200                 205

AAA  AAT  CAG  GCA  AAA  AAT  GCA  GGC  ACC  TCT  ATG  GAC  CCT  TCA  ACA  ACA            773
Lys  Asn  Gln  Ala  Lys  Asn  Ala  Gly  Thr  Ser  Met  Asp  Pro  Ser  Thr  Thr
          210                      215                      220

ACT  TTT  GAT  AAT  ACA  TAT  TAC  AGG  TTG  ATC  CTC  CAA  CAG  AAA  GGC  TTG            821
Thr  Phe  Asp  Asn  Thr  Tyr  Tyr  Arg  Leu  Ile  Leu  Gln  Gln  Lys  Gly  Leu
225                      230                      235                      240

TTT  TCT  TCT  GAT  CAA  GTT  TTG  CTT  GAC  AAC  CCA  GAC  ACT  AAA  AAT  CTG            869
Phe  Ser  Ser  Asp  Gln  Val  Leu  Leu  Asp  Asn  Pro  Asp  Thr  Lys  Asn  Leu
                    245                      250                      255

GTT  GCG  AAG  TTT  GCC  ACC  TCA  AAA  AAG  GCT  TTT  TAT  GAC  GCT  TTT  GCA            917
Val  Ala  Lys  Phe  Ala  Thr  Ser  Lys  Lys  Ala  Phe  Tyr  Asp  Ala  Phe  Ala
               260                      265                      270

AAG  TCC  ATG  ATC  AAA  ATG  AGT  AGC  ATC  AAT  GGT  GGA  CAG  GAG  GTT  AGA            965
Lys  Ser  Met  Ile  Lys  Met  Ser  Ser  Ile  Asn  Gly  Gly  Gln  Glu  Val  Arg
          275                      280                      285

AGG  ACT  GCA  GAG  TGATCAATTA  AAAAGTCTTA  AATTAATTCA  AGTTAAATTG                       1017
Arg  Thr  Ala  Glu
          290

ATGTTTCAAA  CAAGTTAGAA  GTATGAACTT  GTTGGATCAA  ATTTCCTAGA  TGGCAAGATA                   1077

TTATGTCTTT  TTCCTCTATT  AAAGAAATAT  GTATATTTAT  CTGAAGTTAA  TAAATATATC                   1137

ATTTTGATAA  AAAAAAAAAA  AAAAAAAAA                                                         1167
```

( 2 ) INFORMATION FOR SEQ ID NO:17:

( i ) SEQUENCE CHARACTERISTICS:
        ( A ) LENGTH: 313 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met  Ala  Val  Met  Val  Ala  Phe  Leu  Asn  Leu  Ile  Ile  Met  Phe  Ser  Val
-21       -20                      -15                      -10

Val  Ser  Thr  Ser  Lys  Ser  Leu  Ser  Leu  Asn  Tyr  Tyr  Ser  Lys  Thr  Cys
-5                            1                   5                      10

Pro  Asp  Val  Glu  Cys  Ile  Val  Ala  Lys  Ala  Val  Lys  Asp  Ala  Thr  Ala
               15                      20                      25

Arg  Asp  Lys  Thr  Val  Pro  Ala  Ala  Leu  Leu  Arg  Met  His  Phe  His  Asp
          30                      35                      40

Cys  Phe  Val  Arg  Gly  Cys  Gly  Ala  Ser  Val  Leu  Leu  Asn  Ser  Lys  Gly
     45                      50                      55

Ser  Asn  Lys  Ala  Glu  Lys  Asp  Gly  Pro  Pro  Asn  Val  Ser  Leu  His  Ala
```

```
            60                      65                      70                      75

Phe   Tyr   Val   Ile   Asp   Ala   Ala   Lys   Lys   Ala   Leu   Glu   Ala   Ser   Cys   Pro
                                80                      85                      90

Gly   Val   Val   Ser   Cys   Ala   Asp   Ile   Leu   Ala   Leu   Ala   Ala   Arg   Asp   Ala
                        95                      100                     105

Val   Phe   Leu   Ser   Gly   Gly   Pro   Thr   Trp   Asp   Glu   Pro   Lys   Gly   Arg   Lys
                  110                     115                     120

Asp   Gly   Arg   Thr   Ser   Lys   Ala   Ser   Glu   Thr   Arg   Gln   Leu   Pro   Ala   Pro
            125                     130                     135

Thr   Phe   Asn   Leu   Ser   Gln   Leu   Arg   Gln   Ser   Phe   Ser   Gln   Arg   Gly   Leu
      140                     145                     150                           155

Ser   Gly   Glu   Asp   Leu   Val   Ala   Leu   Ser   Gly   Gly   His   Thr   Leu   Gly   Phe
                              160                     165                           170

Ser   His   Cys   Ser   Ser   Phe   Lys   Asn   Arg   Ile   His   Asn   Phe   Asn   Ala   Thr
                        175                     180                     185

His   Asp   Glu   Asp   Pro   Ser   Leu   Asn   Pro   Ser   Phe   Ala   Thr   Lys   Leu   Ile
                        190                     195                     200

Ser   Ile   Cys   Pro   Leu   Lys   Asn   Gln   Ala   Lys   Asn   Ala   Gly   Thr   Ser   Met
                  205                     210                     215

Asp   Pro   Ser   Thr   Thr   Thr   Phe   Asp   Asn   Thr   Tyr   Tyr   Arg   Leu   Ile   Leu
      220                           225                     230                           235

Gln   Gln   Lys   Gly   Leu   Phe   Ser   Ser   Asp   Gln   Val   Leu   Leu   Asp   Asn   Pro
                              240                     245                           250

Asp   Thr   Lys   Asn   Leu   Val   Ala   Lys   Phe   Ala   Thr   Ser   Lys   Lys   Ala   Phe
                        255                     260                     265

Tyr   Asp   Ala   Phe   Ala   Lys   Ser   Met   Ile   Lys   Met   Ser   Ser   Ile   Asn   Gly
                  270                     275                     280

Gly   Gln   Glu   Val   Arg   Arg   Thr   Ala   Glu
            285                     290
```

( 2 ) INFORMATION FOR SEQ ID NO:18:

( i ) SEQUENCE CHARACTERISTICS:
        ( A ) LENGTH: 3341 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

```
TCAATGTCAG   AATGATACTG   ACAGATCTAA   TTTCGGTTAA   TTTGATTACT   AATTAGTAGG         60

TGCCAGTGGC   ATAAATTGAA   TAAGAAATAA   AAATAATTCA   TTATCAATTC   AAATGAAGGA        120

AAAATATATT   GTGTCAAAAG   GATATTAATT   ATCAAGATTC   AAAGGAAAAA   ATAGTATACT        180

CTTTTTTATA   AATACACTAC   TGAGTAATTT   AACCAAATTT   AAATTATAAT   TTAATGCTC         240

AGTTTACTTC   AATGGCTATA   CCTTTTTTTT   ATATATTCAA   TGGCTATACC   TATAAATTGT        300

AATATTCAAG   CATTGTTTTA   ATGGAAGCAA   ACAAGGCATC   ACATATGGCT   AGGAAGAATT        360

GAACAAAAAC   AAATTAGCTA   CATACATTAA   GCTCTTAATA   TTATAAAAAC   ATGCCGATGA        420

TATATGTCCA   TAGATTTCAA   GGGAGCTAAT   ACCGGAAAGT   GTCAAGGATT   TATACTTTAC        480

AGCTAAAGTT   TCAGTCTCAA   AGAAAATGAT   GACACTGTAT   CATTGAGCAG   ACACAATGAG        540

TTACATCACA   AAACCAGCCT   GTAGGGATAC   ATGACTCATA   TTCCTTGTCA   AATATCGCTG        600

CCTCAATGTG   CATAGCGATT   ATAGTAATGG   ATTCACAGTA   AAGGAGCAGG   TAAGCCAATT        660

TTTTATTCTT   AAATTCCCTG   TTGAGACTAC   ATTATATTTT   TGAATTGCGA   GATATTCAAG        720
```

```
GATTACTTGT  TATATATGTT  AAGCCGCCGC  ATACTGTTTA  AAGTATTAAT  GATATATCAT   780

TGTTACTATA  AAATATTTTT  ACACAATGCA  AGGTAAATAT  TTCTATTACA  TGTTGACATA   840

AAAATATCTT  ACGTAAACTA  AACTAAACTC  TTGTTTAAAA  TGGTACTAGT  ATCTATACAA   900

CGAGATTAAA  GCTACAAAAA  TATGATACAA  AGAGGGAGAT  TTTGTATAGT  ATCCTATGCT   960

TGAAGAACGT  ATCAACATCC  AGTATCTCGA  AAATTCAGTA  CTAAAATGTA  AAATCTATTG  1020

ATGTGTACTG  AAGGATTCAG  AAATTCAACT  ATTTTGAACT  CGCTGTATAT  TAATTTGTCC  1080

ATATAAGGTC  ACAGCAGCCA  ACTAATCATT  TTTTATTAG   AGACTAGATA  CAATTATTAC  1140

ATGCAAATGG  ATAATAAAGT  AGCATGTAGC  ATCACCTTAT  CGCACATGTT  AGTTAGCTGC  1200

ATGGACCATC  TGTATGATTT  GTGATGTGTC  TTGTAGCTTA  ACTTAAGCAC  TATATATCAC  1260

TGATCAGTGT  TGTGGAAACA  GCGAAGAGAA  ATGAAATTGC  CTCTTTCAAG  AAGCATCTGA  1320

GTGTTTACTA  TTTTGTACTA  TATTTATATA  TAGTCACTCA  AGCTTCTAGG  ATTTCTGCCT  1380

GCTGCATCAA  AATGGGAAGC  AACTTGAGGT  TTTTGAGTCT  TTGCCTCTTG  GCATTGATTG  1440

CATCAACTCA  TGCTCAACTT  CAGCTTGGTT  TTTATGCTAA  CAGTTGCCCA  AAAGCAGAGC  1500

AAATTGTTTT  GAAATTTGTT  CATGACCATA  TCCACAATGC  TCCATCACTA  GCAGCTGCAT  1560

TAATAAGAAT  GCACTTCCAT  GACTGTTTTG  TAAGGGTATG  TGGTTCAAGC  CTATAATTTT  1620

CTTTCATTTT  TTACTTAACA  AGTACCATAT  ATGTTAGATT  AAAGAACTAA  CTAAGATGAA  1680

GTATTTCAGG  GATGTGATGC  ATCAGTCCTT  CTGAACTCAA  CAACCAATCA  GGCTGAGAAG  1740

AATGCTCCTC  CAAATCTCAC  AGTAAGAGGC  TTTGACTTCA  TTGACAGAAT  AAAGAGCCTT  1800

GTTGAAGCTG  AATGCCCTGG  TGTGGTCTCT  TGTGCTGATA  TCCTCACTTT  GGCTGCCAGA  1860

GACACTATTG  TAGCCACAGT  AAGTACTCAA  TTGCTATCAG  GAAAATCTTA  AGAGTATAAG  1920

CACAACTTCT  GCTTCACCTT  TATATCTTTA  CACTTCTTTT  TGAGAACAAG  ATGACCCATT  1980

TGCTGGTTTA  TGCCATTACT  GACATTGGTG  TTCAGGGTGG  ACCTTTTTGG  AAAGTTCCAA  2040

CTGGTCGAAG  GGATGGGGTC  GTCTCTAACT  TGACGGAAGC  CAGAAATAAC  ATTCCTGCTC  2100

CATTTTCCAA  CTTCACCACC  CTACAGACAC  TCTTTGCTAA  CCAAGGACTT  GATTTGAAGG  2160

ACTTGGTCCT  GCTCTCTGGT  ATCATTTATG  AAACAAATCC  TAAGCATTAT  TGTTGAAAGA  2220

CTAACACGTT  TTTGAGTCCC  TCATGGTAAC  GCCAGGTTTC  CAGTCACGAC  GTTGTAAAAC  2280

GACGGCCAGT  GAGCGCGCAG  TAATACGACT  CACTATAGGC  GAATTGGAGC  TCCAGCGGTG  2340

GCGGCCGCTC  TAGAACTAGT  GGATCCCCCG  GGCTGCAGGT  TTTCGATATC  AAGCTTATCG  2400

ATACCGTCGA  CACCTCGAGT  TGGAAATATG  TCTAAATATC  TGCAATTTCA  ACATGAATAA  2460

TTTATTTTTT  AGGAATTTAT  TAACTACATT  TTAAATTTTC  AGGATATTGA  TTTGATAATT  2520

CTTATTATTT  AGACTTTAGG  ACACTATCAG  TTTGTTTAAT  TTCAAGGTTA  AGATGTGTTA  2580

TATTTTGAAT  TTTGCATTAC  ATTATTTCAT  TTTAAAAAAT  AAAACCAACA  AATTGGCATG  2640

AATTATACAT  TGTTCTTGGG  CTTGTAATGA  GCAAGAGTTC  AAATTGTTTC  AGGTGCTCAC  2700

ACAATTGGTA  TCGCTCATTG  CTCATCATTA  TCAAACCGGT  TGTTCAATTT  CACTGGCAAG  2760

GGTGATCAAG  ACCCGTCACT  AGATAGTGAA  TATGCTGCAA  ATTTGAAAGC  ATTCAAGTGC  2820

ACAGACCTCA  ACAAGTTGAA  CACCACAAAA  ATTGAGATGG  ACCCTGGAAG  TCGCAAGACA  2880

TTTGATCTTA  GCTACTATAG  TCACGTTATT  AAGAGAAGGG  GTCTATTTGA  GTCAGATGCT  2940

GCATTATTGA  CTAACTCAGT  TACAAAGGCA  CAAATCATCC  AATTGCTTGA  AGGGTCAGTT  3000

GAAAATTTCT  TTGCTGAGTT  TGCAACCTCC  ATCGAGAAAA  TGGGAAGAAT  TAATGTGAAG  3060

ACAGGGACAG  AAGGAGAGAT  CAGGAAGCAT  TGTGCATTTA  TAAATAGCTA  AGAATCTTGT  3120
```

| | | | | | |
|---|---|---|---|---|---|
| CTTGTTCATG | GATGAATCTT | GTATCATTTA | TTTTTGGGG | TTTGATTATT | TATGCTATGC | 3180 |
| CATGTTTTTT | GATTAGTTAT | GCTATGCCAT | GTGGTCTCTG | TCTACATACG | TGTGATCCTT | 3240 |
| TATGGTATGG | TTGTTGTATG | TGTGTTGGAA | TAAGTGGGCT | CTTAAGTTAT | TCATATTTCC | 3300 |
| AACTTTGCTG | GTAGATCATG | CTCTTGTAAT | AAGAACCAGA | A | | 3341 |

( 2 ) INFORMATION FOR SEQ ID NO:19:

( i ) SEQUENCE CHARACTERISTICS:
        ( A ) LENGTH: 2404 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

| | | | | | |
|---|---|---|---|---|---|
| CAATAATTAT | AGTTTGATAG | CCTGCTACCA | TCAAGGATTG | CAATGCAAGC | TTTGGCACCA | 60 |
| AAAACAAAAT | TACGATGGCT | CAACCTCAAC | CTTAACTACC | GCATACATTG | GTATAACTCA | 120 |
| GGCGCAGTTT | GGTTTGCTAG | TGAAACCACT | AGTGATTTGG | TTAGTGCTGA | TCAGACTTTG | 180 |
| AGTGACTTTT | TTATGTCGTG | CCATTTTCAA | TTAAATGTCT | AAAAATTTTA | AGATAATTAA | 240 |
| ACAACTTTTT | TATTTTTAAA | AAGCTAAAAC | ACAAAAGAA | ATGAGTACTT | TTCTTGTAAA | 300 |
| TTGACAATAA | TGGTTTTTTT | TATAAAAAAA | AAAATAAGTG | TCTTACAAAA | GAAAATTATC | 360 |
| CAAACATAAC | ACTAATATGG | CATGGACAAT | TGGCCACGAG | GCTGTTGGCC | TCAATTTCCG | 420 |
| TTGAAAAGCC | TAAACTGAAA | TATGGCAAGA | GTTTGATCAC | AGAAAAAAAT | GGTCGGGGTA | 480 |
| AAATCAAACT | TTCACTTATT | ACATTAGGAC | AATAGGAGAA | AGACCAAGGA | TAATGTCATA | 540 |
| ATCAACGAAT | CATAATTATG | TATCATGGGG | TGGAGGATGA | CATCGTGATT | TGTGATATTA | 600 |
| CCAACTACTC | TTGAAGAGTT | TAGACCATGA | AACTATAGCT | TAAGACTGGA | TTTAGCATGA | 660 |
| ATATGTAATT | AAATTATTCT | GGATCGAGAG | TAACATACCA | ATAAAAAAAA | AGAAGAGGA | 720 |
| ACATCACAAG | CCACAGAAAG | CTACCGGAGG | CTTAAAAAGT | TTAAGGTTCA | TTAGGACGGA | 780 |
| GCATAAAGTG | GATTGTCTTT | TAGTAATGAG | AATGCTTCAA | CATTACTACT | CTTGATTGAC | 840 |
| AGTACTTCTT | AACGAATTGA | TTTCTAGGGC | CACATTATCT | CAAACAATAA | TTGATCTCTT | 900 |
| TTATATCTAT | AAAAATTCAT | TTTCCCCATC | TTTGATTTCC | ACGGCTAAAA | GCTAAATATC | 960 |
| ATCAAAGTAC | TCAAATTAGC | ATGGCTGTCA | TGGTTGCATT | CTTGAATTTG | ATCATCATGT | 1020 |
| TTTCAGTAGT | CTCTACAACA | GGCAAGTCAC | TGAGCTTAAA | CTACTATGCA | AAAACATGCC | 1080 |
| CTAATGTGGA | GTTCATTGTT | GCCAAGGCAG | TAAAGGATGC | CACTGCTAGG | AAAAAACTGT | 1140 |
| TCCAGCAGCA | ATTCTGCGAA | TGCACTTCCA | TGATTGTTTC | GTTCGGGTAA | TGCTATTTTG | 1200 |
| ACCCCTCCTC | CCTCCTTTCC | TCTTGACCGT | TCCGCCTCAT | TTGATGCATC | ATGAAATCAA | 1260 |
| ATCATATTGT | TTTCTTTTTT | CCTATACTCT | TGAAGGGGTG | TGATGCCTCT | GTGCTGCTAA | 1320 |
| ATTCAAAAGG | AAACAACAAA | GCAGAAAAAG | ACGGGCCACC | AAATGTTTCT | TTGCATGCAT | 1380 |
| TCTATGTCAT | TGATGCAGCA | AAGAAAGCAC | TAGAAGCTTC | ATGCCCTGGT | GTGGTCTCTT | 1440 |
| GTGCTGACAT | CTCTGCTCTG | GCAGCAAGGG | TCGCAGTTTT | TCTGGTAAGA | AAACTTTGAA | 1500 |
| AAGTACCAAA | TTTCTCATCA | TTCAGATCCT | AAACTAAACA | ATCATTATGT | CTTCGAGAAT | 1560 |
| TGACAAATGC | AGCTAAGGTG | GCTTGTATTT | GGAAGTCTTG | ACTAATTGTA | TAAAATATAT | 1620 |
| TCTGCAGTCA | GGAGGACCTA | CATGGGATGT | TCCTAAAGGA | AGAAGGATG | GTAGAACATC | 1680 |
| TAAAGCCAGT | GAAACCAGAC | AATTGCCAGC | ACCAACCTTC | AACTTATCAC | AACTGCGGCA | 1740 |

-continued

| | | | | | | |
|---|---|---|---|---|---|---|
| AAGTTTCTCT | CAAAGAGGAC | TGTCAGGGGA | AGACCTGGTA | GCTCTGTCAG | GTAAGCTATT | 1800 |
| CCTAAAGTCA | AAACTGCCAA | AACTTGACCA | TTTTTCATTT | ATTCCAATTT | ATATCTGAAT | 1860 |
| AGAGTTTAGA | GTTTCTCCTT | TGACTCATAT | GTAGGGGGGC | ACACTTTGGG | TTTCTCTCAC | 1920 |
| TGCTCATCTT | TCAAGAACAG | AATCCACAAC | TTCAATGCAA | CACATGATGT | TGACCCTTCA | 1980 |
| TTAAATCCAT | CATTTGCAGC | AAAACTGATC | TCAATTTGTC | CACTAAAAAA | TCAGGCAAAA | 2040 |
| AATGCAGGCA | CCTCTATGGA | CCCTTCAACA | ACAACTTTTG | ATAATACATA | TTACAGGTTG | 2100 |
| ATCCTCCAAC | AGAAAGGCTT | GTTTTCTTCT | GATCAAGTTT | TGCTTGACAA | CCCAGACACT | 2160 |
| AAAAATCTGG | TTACAAAGTT | TGCCACCTCA | AAAAAGGCTT | TTTATGAGGC | TTTTGCGAAG | 2220 |
| TCCATGATCA | GAATGAGTAG | CTACAATGGT | GGACAGGAGG | TTAGAAGGAC | TGCTGAATGA | 2280 |
| TCAATTAATA | AGTCTTAAAT | CAATTCAAGT | TAAATTGATG | TTCCAAACAA | GTTGGATCAA | 2340 |
| ATTTCCTAGA | TGCCAAGAAT | ATTATGTCTT | TTTCCTCTAT | TAAAGAAATA | TGTATATTTA | 2400 |
| TCTG | | | | | | 2404 |

What is claimed is:

1. An isolated DNA consisting of a nucleic acid having the sequence set forth in SEQ ID NO:18 or SEQ ID NO:19.

2. An isolated DNA consisting of the promoter for a soybean peroxidase having a nucleic acid sequence corresponding to nucleotides 1-1391 of SEQ ID NO:18 or a nucleic acid sequence corresponding to nucleotides 1-980 of SEQ ID NO:19.

* * * * *